US012651644B2

(12) United States Patent
Shao et al.

(10) Patent No.: US 12,651,644 B2
(45) Date of Patent: Jun. 9, 2026

(54) APPLICATION OF GENE MARKERS IN MULTI-CANCER EARLY DETECTION, METHOD FOR CONSTRUCTING EARLY DETECTION MODEL, AND DETECTION DEVICE

(71) Applicant: Geneseeq Technology Inc., Toronto (CA)

(72) Inventors: Yang Shao, Jiangsu (CN); Hua Bao, Jiangsu (CN); Min Wu, Jiangsu (CN); Shiting Tang, Jiangsu (CN); Xiaoxi Chen, Jiangsu (CN); Shuyu Wu, Jiangsu (CN); Rui Liu, Jiangsu (CN); Xue Wu, Jiangsu (CN)

(73) Assignee: Geneseeq Technology Inc., Toronto (CA)

( * ) Notice: Subject to any disclaimer, the term of this patent is extended or adjusted under 35 U.S.C. 154(b) by 0 days.

(21) Appl. No.: 18/945,348

(22) Filed: Nov. 12, 2024

(65) Prior Publication Data

US 2025/0391503 A1 Dec. 25, 2025

(30) Foreign Application Priority Data

Jun. 19, 2024 (CN) .......................... 202410791117.X

(51) Int. Cl.
| | |
|---|---|
| *G16B 20/20* | (2019.01) |
| *G16B 20/10* | (2019.01) |
| *G16B 30/10* | (2019.01) |
| *G16B 40/20* | (2019.01) |

(Continued)

(52) U.S. Cl.
CPC ............. *G16B 20/20* (2019.02); *G16B 20/10* (2019.02); *G16B 30/10* (2019.02); *G16B 40/20* (2019.02); *G16H 10/60* (2018.01); *G16H 50/20* (2018.01)

(58) Field of Classification Search
None
See application file for complete search history.

(56) References Cited

PUBLICATIONS

Wan, Nathan, et al. "Machine learning enables detection of early-stage colorectal cancer by whole-genome sequencing of plasma cell-free DNA." BMC cancer 19.1 (2019): 832. (Year: 2019).*

(Continued)

*Primary Examiner* — Karlheinz R. Skowronek
*Assistant Examiner* — Mary C Leverett
(74) *Attorney, Agent, or Firm* — JCIPRNET

(57) ABSTRACT

The present disclosure relates to an application of gene markers in multi-cancer early detection, a method for constructing an early detection model, and a detection device. In the present disclosure, low-coverage whole-genome sequencing is conducted on cell-free DNAs (cfDNAs) from a plasma sample, and according to high-throughput sequencing results, six differential features of the cfDNA fragments are analyzed for each cancer. Then the training and modeling are conducted with a convolutional neural network to allow the early detection of a plurality of cancers at a low sequencing depth. Then the training and modeling are conducted with a generalized linear model (GLM), a gradient boosting machine, a random forest model, a deep learning model, and an extreme gradient boosting model, and staking is conducted with a GLM to construct a multi-feature algorithm, to allow the tissue-of-origin-based detection of cancers.

4 Claims, 8 Drawing Sheets

(51) Int. Cl.
    *G16H 10/60*          (2018.01)
    *G16H 50/20*          (2018.01)

(56)                    References Cited

PUBLICATIONS

Jamshidi, Arash, et al. "Evaluation of cell-free DNA approaches for multi-cancer early detection." Cancer Cell 40.12 (2022): 1537-1549. (Year: 2022).*

Peneder, Peter, et al. "Multimodal analysis of cell-free DNA whole-genome sequencing for pediatric cancers with low mutational burden." Nature communications 12.1 (2021): 3230. (Year: 2021).*

* cited by examiner

APPLICATION OF GENE MARKERS IN MULTI-CANCER EARLY DETECTION, METHOD FOR CONSTRUCTING EARLY DETECTION MODEL, AND DETECTION DEVICE

CROSS-REFERENCE TO RELATED APPLICATION

This application claims the priority benefit of China application serial no. 202410791117.X, filed on Jun. 19, 2024. The entirety of the above-mentioned patent application is hereby incorporated by reference herein and made a part of this specification.

BACKGROUND

Technical Field

The present disclosure relates to an application of gene markers in multi-cancer early detection, a method for constructing an early detection model, and a detection device, and belongs to the technical field of molecular biomedicine.

Description of Related Art

Traditional methods for the early screening of cancer have many limitations, and there is a lack of effective early screening methods for many cancers. Cholangiocarcinoma, endometrial cancer, liver cancer, ovarian cancer, and pancreatic cancer are mostly screened by magnetic resonance imaging (MRI) and computed tomography (CT). Esophageal cancer, gastric cancer, and nasopharyngeal carcinoma are mostly screened by endoscopy. Cervical cancer is mostly detected by a cervical smear. Lymphoma is mostly detected by blood or bone marrow. The above screening methods have problems such as high radioactivity, inconvenience, and even causing pain, resulting in low compliance of screening. The endoscopic screening can discover cancer at an early stage. However, the endoscopic screening is an invasive screening method that involves a painful examination process and has high requirements for the physique of a patient. As a result, the endoscopic screening is not included in the routine physical examination items, resulting in low screening prevalence. The imaging methods are usually radioactive and have a low recognition ability for early-stage cancer. The tissue biopsy involves difficult sampling and is prone to incomplete sampling due to tumor heterogeneity, which is not conducive to diagnostic classification and is easy to cause complications. In addition, the tissue biopsy has relatively-high false positive and negative rates. There is a lack of recommended standard screening methods for these cancers. For cancers that lack recommended standard screening methods, a multi-cancer detection model can be adopted as an effective complement to standard screening. The multi-cancer detection model covers a variety of cancers that lack standard screening methods, and can accurately detect corresponding tissue origins to improve the efficiency of cancer screening. Currently, there are recommended gold standard screening methods merely for breast cancer, lung cancer, and intestinal cancer. The standard screening method for breast cancer is mammography. The standard screening method for lung cancer is low-dose computed tomography (LDCT). The standard screening method for prostate cancer is prostate-specific antigen (PSA) detection. Studies have shown that the compliance of mammography is 49.7%, the compliance of LDCT is 55%, and the compliance of PSA detection is 50.4%. Although these cancers have recommended standard screening methods, there are still shortcomings such as low compliance, limited detectability for early-stage cancer, and some limitations on large-scale population screening. The multi-cancer detection model has obvious advantages over the traditional screening methods. A detection object of the multi-cancer detection model is blood, which is easy to collect. Therefore, the multi-cancer detection model can reduce the trauma and risk of patients, improve the compliance, increase a detection rate of early-stage patients, and allow the early treatment, thereby improving a 5-year survival rate of patients.

SUMMARY

In the present disclosure, low-coverage whole-genome sequencing (WGS) is conducted on cell-free DNAs (cfDNAs) from a plasma sample, and according to high-throughput sequencing results, six differential features of the cfDNA fragments are analyzed for each cancer, including genome-wide fragment size coverage (FSC), fragment size distribution (FSD) on long and short arms of each chromosome, 1 MB bin fragment copy number variation (1 Mb-bin CNV), nucleosome profile (NP), fragment-based methylation (FM), and mutational context (MC)/mutational signature (MS). Then these features are input into a convolutional neural network (CNN) to construct a multi-cancer detection model, and the five algorithms of a generalized linear model (GLM), a gradient boosting machine (GBM), a random forest (RF) model, a deep learning (DL) model, and an extreme gradient boosting (XGBoost) model are integrated to construct a multi-cancer tissue-of-origin (TOO) model including a plurality of features and a plurality of algorithms. As a result, the present disclosure can allow the non-invasive accurate detection and TOO tracing for a plurality of cancers at a low depth, with high specificity and high sensitivity.

The present disclosure provides an application of gene markers in preparation of a multi-cancer early detection reagent. The multi-cancer early detection reagent is used to distinguish cancer patients of a plurality of cancers from healthy people; or, the multi-cancer early detection reagent is used to allow TOO-based classification of cancers in the cancer patients of the plurality of cancers;

the plurality of cancers refer to cholangiocarcinoma, breast cancer, cervical cancer, intestinal cancer, endometrial cancer, esophageal cancer, gastric cancer, nasopharyngeal carcinoma, lung cancer, liver cancer, lymphoma, ovarian cancer, pancreatic cancer, or prostate cancer; and the gene markers include:

a first marker: proportions of short reads and long reads in different windows of a reference genome to which cfDNA fragments are aligned;

a second marker: quantities of reads in different length gradient intervals on long arms and short arms of the reference genome to which the cfDNA fragments are aligned, where the different length gradient intervals refer to different length gradient ranges produced by increasing at a set step size progressively in a range of 100 bp to 220 bp, and the long arms and the short arms are selected from the group consisting of the following chromosome arms:

chr1_p, chr4_q, chr8_p, chr11_q, chr16_q, chr20_p, chr1_q, chr5_p, chr8_q, chr12_p, chr17_p, chr20_q, chr2_p, chr5_q, chr9_p, chr12_q, chr17_q, chr21_q,

3 chr2_q, chr6_p, chr9_q, chr13_q, chr18_p, chr22_q, chr3_p, chr6_q, chr10_p, chr14_q, chr18_q, chr3_q, chr7_p, chr10_q, chr15_q, chr19_p, chr4_p, chr7_q, chr11_p, chr16_p, and chr19_q, where a character chr+a number behind the character chr represents a chromosome number, q represents a long arm, and p represents a short arm;

a third marker: copy numbers in different windows on chromosomes in WGS data;

a fourth marker: NP;

a fifth marker: proportions of tribase motifs at broken cytosine-phosphate-guanine (CpG) sites; and a sixth marker: an MC/MS combination;

The first marker is obtained through the following steps: aligning read data to the reference genome, dividing the reference genome into a plurality of windows, and acquiring proportions of short reads and long reads in each of the plurality of windows.

The short reads refer to reads with a length of 100 bp to 150 bp.

The long reads refer to reads with a length of 151 bp to 220 bp.

The second marker is obtained through the following steps:

aligning the cfDNA fragments to the reference genome, and with the long arms and the short arms of chromosomes as regional ranges, acquiring quantities of reads in the different length gradient intervals in each of the regional ranges.

The set step size is 5 bp.

The third marker is obtained through the following steps: dividing the reference genome into a plurality of windows, and acquiring copy number data in different ones of the plurality of windows on chromosomes 1 to 22 in the WGS data.

The fourth marker is obtained through the following steps:

acquiring transcription factors from a gene transcription regulation database (GTRD), and excluding transcription factors without a known transcription site in a catalog of inferred sequence binding preferences (CIS-BP) database;

with a range of −5 kb to +5 kb from a transcription site of each remaining transcription factor as a window, acquiring fragments with a length of 100 bp to 220 bp capable of being aligned to the window, and conducing guanine-cytosine (GC) correction and sequencing depth smoothing successively on read data in the window to obtain a profile curve of each remaining transcription factor; and for each remaining transcription factor, acquiring three features together as the NP as follows:

1) for all transcription sites of each remaining transcription factor, calculating an average depth from 1 kb at an upper end to 1 kb at a lower end of each of the transcription sites;

2) for the profile curve, calculating an amplitude value of a curve trough as a central depth of each remaining transcription factor; and 3) conducting fast Fourier transform on the profile curve of each remaining transcription factor to obtain an amplitude value of a peak point of a nucleosome amplitude signal.

The fifth marker is obtained through the following steps:

1) acquiring read proportions of NCG motifs and CGN motifs at breaks in the broken CpG sites and a ratio of the read proportions, where the read proportions each are obtained as follows: calculating a proportion of reads at each site including a specific base segment in a depth of the site, and then taking an average proportion of the specific base segment at all sites as a read proportion of the specific base segment; and the ratio refers to a ratio of a total read proportion of all base segments of NCG to a total read proportion of all base segments of CGN; and 2) acquiring the read proportions of the NCG motifs and the CGN motifs at a break in each of the CpG sites in two tandem broken CpG dinucleotide sites and a ratio of the read proportions, and combining the read proportions and the ratio of the read proportions to obtain the fifth marker.

The sixth marker is obtained through the following steps:

acquiring single-base mutation information on the cfDNA fragments, and further acquiring 96 single-base substitutions (SBSs) of the tribase motifs and contexts of the 96 SBSs as MCs in the case of removing single nucleotide polymorphisms (SNPs);

acquiring the single-base mutation information on the cfDNA fragments, further acquiring 96 SBSs of the tribase motifs and contexts of the 96 SBSs in the case of not removing the SNPs, and conducting non-negative matrix factorization (NMF) to obtain MSs; and combining the MCs and the MSs to obtain the sixth marker.

The NMF refers to calculation with SigProfilerMatrixGeneratorR of an R package to obtain 79 MSs associated with non-sequencing interference factors.

The present disclosure also provides a method for constructing a multi-cancer early detection model. The multi-cancer early detection model is used to distinguish cancer patients of a plurality of cancers from healthy people. The method includes the following steps:

step 1, extracting cfDNAs from samples of a positive group and a control group, and sequencing to obtain read data;

step 2, aligning the read data to a reference genome, dividing the reference genome into a plurality of windows, and acquiring proportions of short reads and long reads in each of the plurality of windows as a first feature set;

step 3, aligning the read data to the reference genome, and with long arms and short arms of chromosomes as regional ranges, acquiring quantities of reads in different length gradient intervals in each of the regional ranges as a second feature set, where the different length gradient intervals refer to different length gradient ranges produced by increasing at a set step size progressively in a range of 100 bp to 220 bp, and the long arms and the short arms are selected from the group consisting of the following chromosome arms:

chr1_p, chr4_q, chr8_p, chr11_q, chr16_q, chr20_p, chr1_q, chr5_p, chr8_q, chr12_p, chr17_p, chr20_q, chr2_p, chr5_q, chr9_p, chr12_q, chr17_q, chr21_q, chr2_q, chr6_p, chr9_q, chr13_q, chr18_p, chr22_q, chr3_p, chr6_q, chr10_p, chr14_q, chr18_q, chr3_q, chr7_p, chr10_q, chr15_q, chr19_p, chr4_p, chr7_q, chr11_p, chr16_p, and chr19_q, where a character chr+a number behind the character chr represents a chromosome number, q represents a long arm, and p represents a short arm;

step 4, dividing the reference genome into a plurality of windows, and acquiring copy number data in different ones of the plurality of windows on the chromosomes in WGS data as a third feature set;

step 5, acquiring transcription factors from a GTRD, and excluding transcription factors without a known transcription site in a CIS-BP database to obtain 854 transcription factors in total;

with a range of −5 kb to +5 kb from a transcription site of each remaining transcription factor as a window, acquiring fragments with a length of 100 bp to 220 bp capable of being aligned to the window, and conducing GC correction and sequencing depth smoothing successively on read data in the window to obtain a profile curve of each remaining transcription factor; and for each remaining transcription factor, acquiring three feature sets together as a fourth feature set as follows:

1) for all transcription sites of each remaining transcription factor, calculating an average depth from 1 kb at an upper end to 1 kb at a lower end of each of the transcription sites;

2) for the profile curve, calculating an amplitude value of a curve trough as a central depth of each remaining transcription factor; and 3) conducting fast Fourier transform on the profile curve to obtain an amplitude value of a peak point of a nucleosome amplitude signal;

step 6, 1) acquiring read proportions of NCG motifs and CGN motifs at breaks in broken CpG sites and a ratio of the read proportions, where the read proportions each are obtained as follows: calculating a proportion of reads at each site comprising a specific base segment in a depth of the site, and then taking an average proportion of the specific base segment at all sites as a read proportion of the specific base segment; and the ratio refers to a ratio of a total read proportion of all base segments of NCG to a total read proportion of all base segments of CGN; and 2) acquiring the read proportions of the NCG motifs and the CGN motifs at breaks in each of the CpG sites in two tandem broken CpG dinucleotide sites and the ratio of the read proportions, and combining the read proportions and the ratio of the read proportions to obtain a fifth feature set; and step 7, acquiring single-base mutation information on the cfDNAs, and further acquiring 96 SBSs of tribase motifs and contexts of the 96 SBSs as MCs in the case of removing SNPs; acquiring the single-base mutation information on the cfDNAs, further acquiring 96 SBSs of the tribase motifs and contexts of the 96 SBSs in the case of not removing the SNPs, and conducting NMF to obtain MSs; and combining the MCs and the MSs to obtain a sixth feature set; and step 8, taking the first feature set, the second feature set, the third feature set, the fourth feature set, the fifth feature set, and the sixth feature set as initial eigenvalues, inputting the initial eigenvalues as model eigenvectors into a CNN model, and with cancer-developing probability results as output values, training the CNN model to obtain the multi-cancer early detection model.

The step 2 includes: step 2-1, dividing the reference genome into the plurality of windows, and acquiring quantities of the short reads and the long reads in each of the plurality of windows; and step 2-2, normalizing the quantities of the short reads and the long reads in all the plurality of windows of the step 2-1, and taking the proportions of the short reads and the long reads produced after the normalizing as the first feature set.

In the step 2-1, the plurality of windows each have a size of 5 Mb, and the reference genome is divided into 541 windows in total.

The short reads each have a length of 100 bp to 150 bp and the long reads each have a length of 151 bp to 220 bp.

In the step 3, the set step size is 4 bp.

The plurality of windows in the step 4 each have a size of 1 Mb.

In the step 8, the initial eigenvalues also need to be simplified and then used as the model eigenvectors to construct the multi-cancer early detection model. The simplification means that eigenvalues with significant differences between samples of the positive group and the control group are selected from the first feature set, the second feature set, the third feature set, the fourth feature set, the fifth feature set, and the sixth feature set.

The multi-cancer early detection model is further used to allow TOO-based classification of cancers in the cancer patients of the plurality of cancers.

The method further includes: step 9, taking the first feature set, the second feature set, the third feature set, the fourth feature set, the fifth feature set, and the sixth feature set as the initial eigenvalues, inputting the initial eigenvalues as the model eigenvectors into different classifier models, and training the different classifier models to obtain a plurality of subclassifier models for the first feature set, the second feature set, the third feature set, the fourth feature set, the fifth feature set, and the sixth feature set, respectively; and conducting stacking on the plurality of subclassifier models in combination to obtain a TOO-based classification model.

The different classifier models are one or more selected from the group consisting of a generalized linear regression model, a GBM, an RF model, a DL neural network model, and an XGBoost model, and a GLM is adopted for the stacking.

In the step 9, the initial eigenvalues also need to be simplified and then used as the model eigenvectors to construct the TOO-based classification model. The simplification means that eigenvalues with significant differences between samples of the positive group and the control group are selected from the first feature set, the second feature set, the third feature set, the fourth feature set, the fifth feature set, and the sixth feature set.

The present disclosure also provides a multi-cancer early detection device obtained based on the method described above. The multi-cancer early detection device includes:

a sequencing module configured to extract cfDNAs from samples of a positive group and a control group, and sequence the cfDNAs to obtain read data;

a first feature set acquisition module configured to align the read data to a reference genome, divide the reference genome into a plurality of windows, and acquire proportions of short reads and long reads in each of the plurality of windows as a first feature set;

a second feature set acquisition module configured to align the read data to the reference genome, and with long arms and short arms of chromosomes as regional ranges, acquire quantities of reads in different length gradient intervals in each of the regional ranges as a second feature set, where the different length gradient intervals refer to different length gradient ranges produced by increasing at a set step size progressively in a range of 100 bp to 220 bp, and the long arms and the short arms are selected from the group consisting of the following chromosome arms: chr1_p, chr4_q, chr8_p, chr11_q, chr16_q, chr20_p, chr1_q, chr5_p, chr8_q, chr12_p, chr17_p, chr20_q, chr2_p, chr5_q, chr9_p, chr12_q, chr17_q, chr21_q, chr2_q, chr6_p, chr9_q, chr13_q, chr18_p, chr22_q, chr3_p, chr6_q, chr10_p, chr14_q, chr18_q, chr3_q, chr7_p, chr10_q, chr15_q, chr19_p, chr4_p, chr7_q, chr11_p, chr16_p, and chr19_q, where a character chr+a number behind the character chr represents a chromosome number, q represents a long arm, and p represents a short arm;

a third feature set acquisition module configured to divide the reference genome into a plurality of windows, and acquire copy number data in different ones of the plurality of windows on the chromosomes in WGS data as a third feature set;

a fourth feature set acquisition module configured to acquire transcription factors from a GTRD, and exclude transcription factors without a known transcription site in a CIS-BP database to obtain 854 transcription factors; with a range of −5 kb to +5 kb from a transcription site of each remaining transcription factor as a window, acquire fragments with a length of 100 bp to 220 bp capable of being aligned to the window, and conduct GC correction and sequencing depth smoothing successively on read data in the window to obtain a profile curve of each remaining transcription factor; and for each remaining transcription factor, acquire three feature sets together as a fourth feature set as follows: 1) for all transcription sites of each remaining transcription factor, calculate an average depth from 1 kb at an upper end to 1 kb at a lower end of each transcription site; 2) for the profile curve, calculate an amplitude value of a curve trough as a central depth of each remaining transcription factor; and 3) conduct fast Fourier transform on the profile curve to obtain an amplitude value of a peak point of a nucleosome amplitude signal;

a fifth feature set acquisition module configured to: 1) acquire read proportions of NCG motifs and CGN motifs at breaks in broken CpG sites and a ratio of the read proportions, where the read proportions each are obtained as follows: calculating a proportion of reads at each site comprising a specific base segment in a depth of the site, and then taking an average proportion of the specific base segment at all sites as a read proportion of the specific base segment; and the ratio refers to a ratio of a total read proportion of all base segments of NCG to a total read proportion of all base segments of CGN; and 2) acquire the read proportions of the NCG motifs and the CGN motifs at a break in each of the CpG sites in two tandem broken CpG dinucleotide sites and the ratio of the read proportions, and combine the read proportions and the ratio of the read proportions to obtain the fifth marker;

a sixth feature set acquisition module configured to acquire single-base mutation information on the cfDNAs, and further acquire 96 SBSs of tribase motifs and contexts of the 96 SBSs as MCs in the case of removing SNPs; acquire the single-base mutation information on the cfDNAs, further acquire 96 SBSs of the tribase motifs and contexts of the 96 SBSs in the case of not removing the SNPs, and conduct NMF to obtain MSs; and combine the MCs and the MSs to obtain a sixth feature set; and a sample classification module configured to take the first feature set, the second feature set, the third feature set, the fourth feature set, the fifth feature set, and the sixth feature set as initial eigenvalues, input the initial eigenvalues as model eigenvectors into a CNN model, and with cancer-developing probability results as output values, train the CNN model to obtain the multi-cancer early detection model.

The multi-cancer early detection model further includes a first simplification module configured to simplify the initial eigenvalues to obtain the model eigenvectors. The simplification means that eigenvalues with significant differences between samples of the positive group and the control group are selected from the first feature set, the second feature set, the third feature set, the fourth feature set, the fifth feature set, and the sixth feature set.

The multi-cancer early detection model further includes a TOO model configured to allow TOO-based classification of cancers in the cancer patients of the plurality of cancers. The TOO model is further configured to take the first feature set, the second feature set, the third feature set, the fourth feature set, the fifth feature set, and the sixth feature set as initial eigenvalues, input the initial eigenvalues as model eigenvectors into different classifier models, and train the classifier models to obtain a plurality of subclassifier models for the first feature set, the second feature set, the third feature set, the fourth feature set, the fifth feature set, and the sixth feature set, respectively; and conduct stacking on the plurality of subclassifier models to obtain a TOO-based classification model.

The multi-cancer early detection device further includes a second simplification module configured to simplify the initial eigenvalues to obtain the model eigenvectors. The simplification means that eigenvalues with significant differences between samples of the positive group and the control group are selected from the first feature set, the second feature set, the third feature set, the fourth feature set, the fifth feature set, and the sixth feature set.

Advantages: The early detection model constructed in the present disclosure can allow the early detection of a plurality of cancers, and can distinguish 14 tumors simultaneously.

DESCRIPTION OF THE EMBODIMENTS

Figure 1:
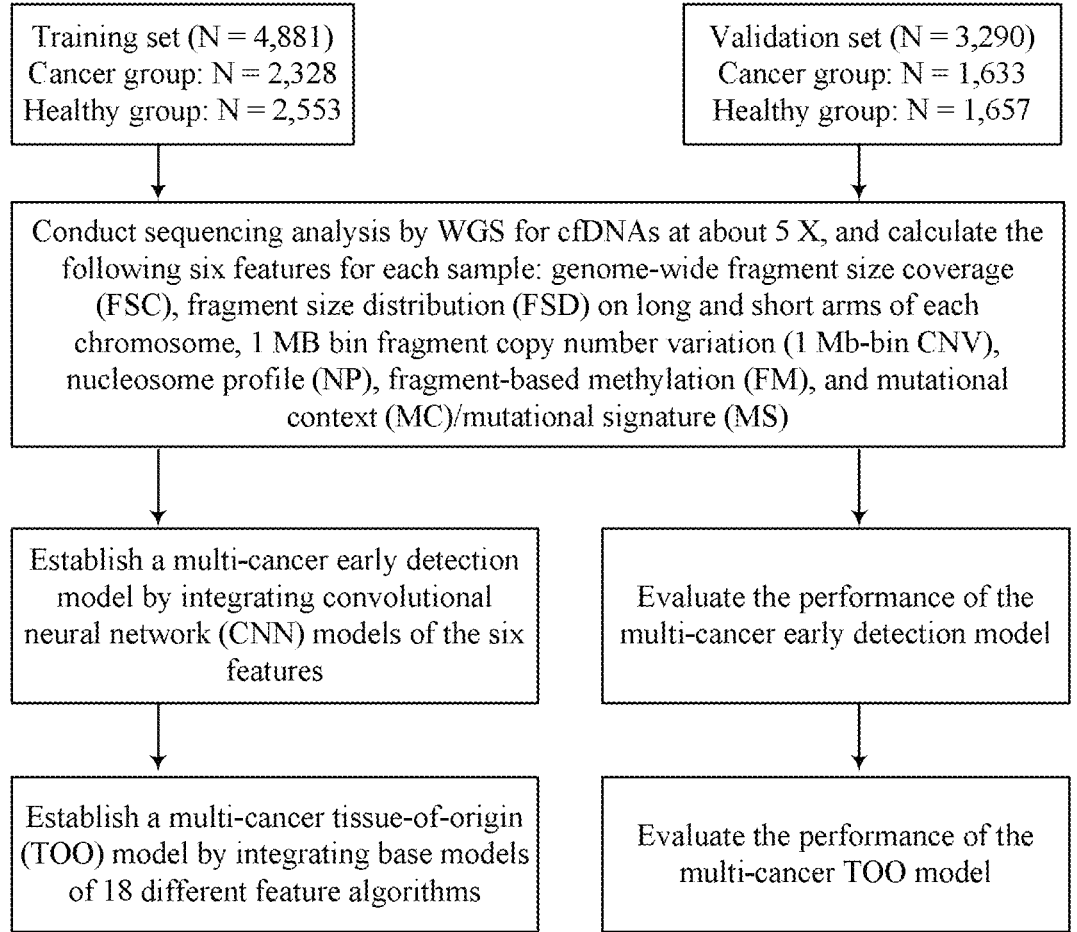
FIG. 1 is a schematic diagram of a model construction process.
Figure 2:
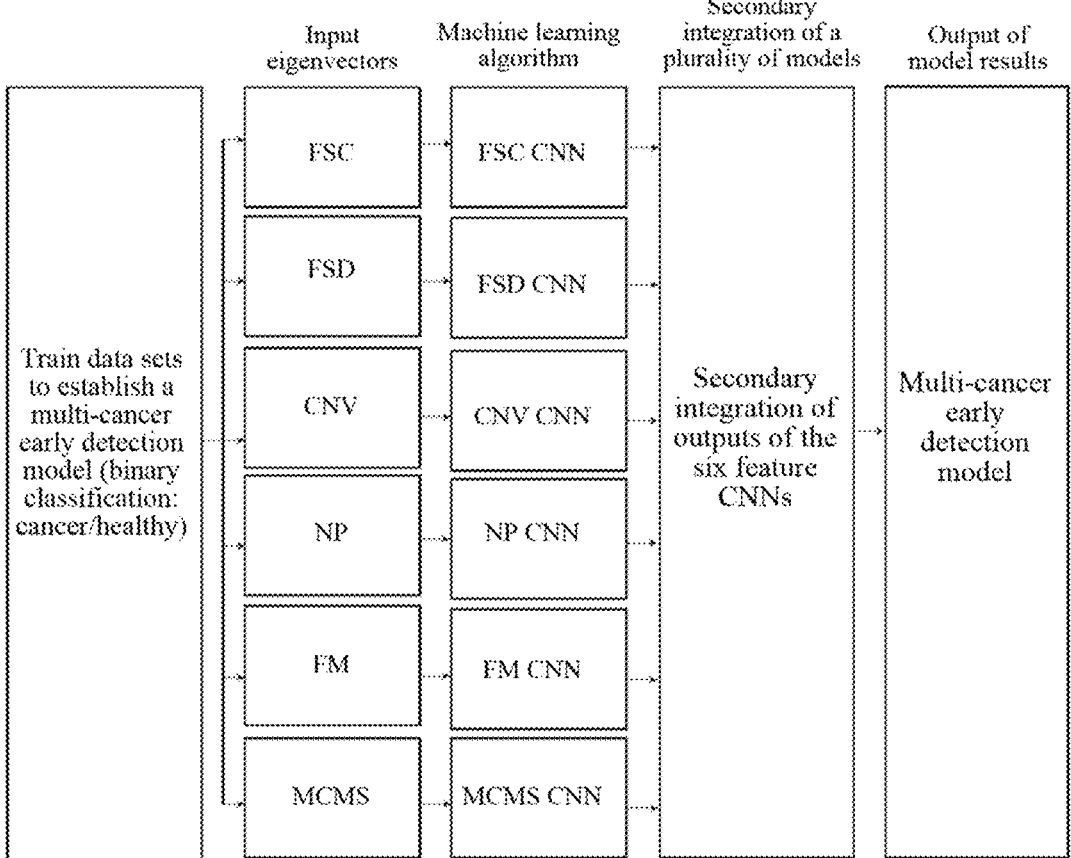
FIG. 2 is a schematic diagram of a process for constructing a multi-cancer early detection model.
Figure 3:
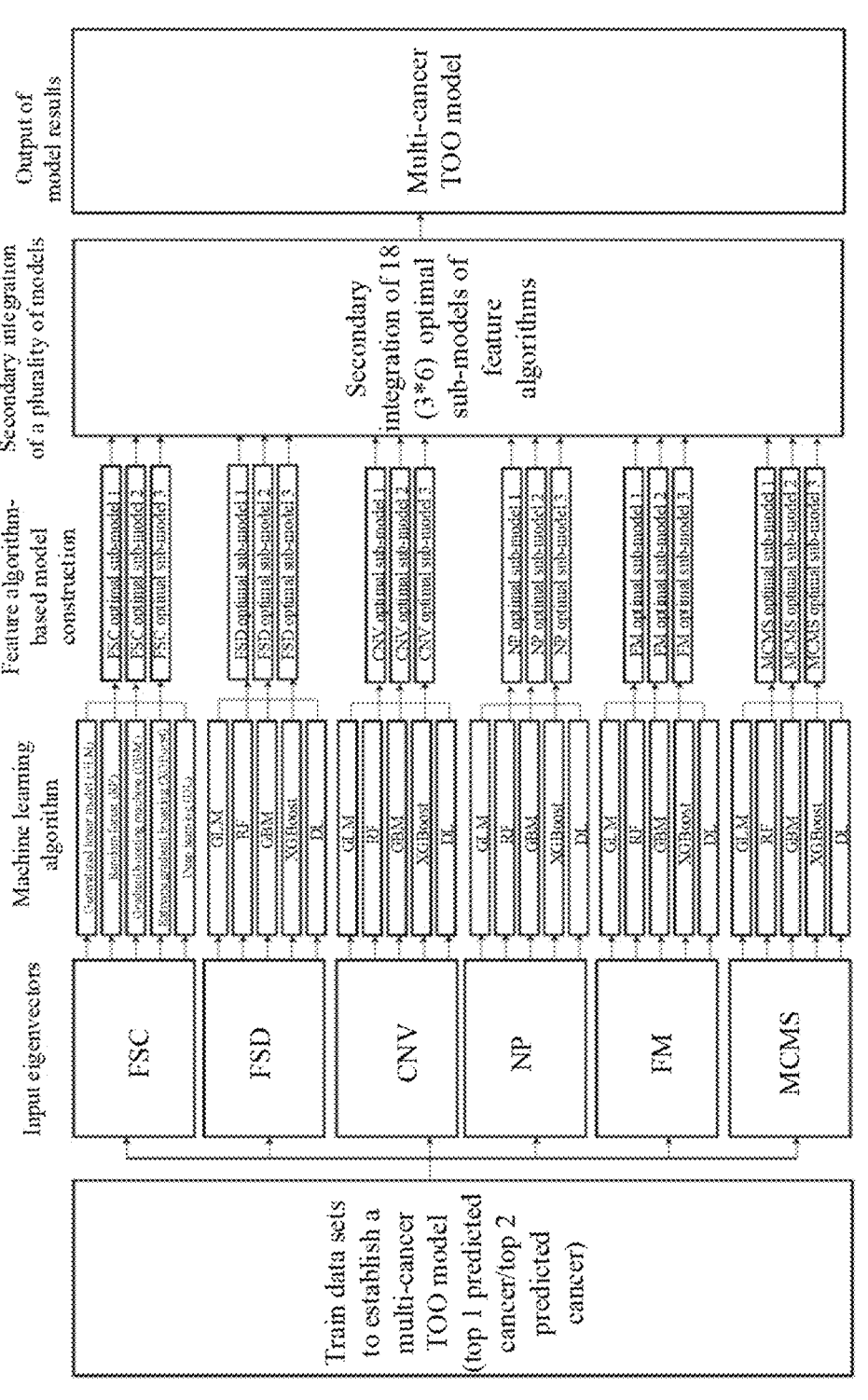
FIG. 3 is a schematic diagram of a process for constructing a multi-cancer TOO model.
Figure 4:
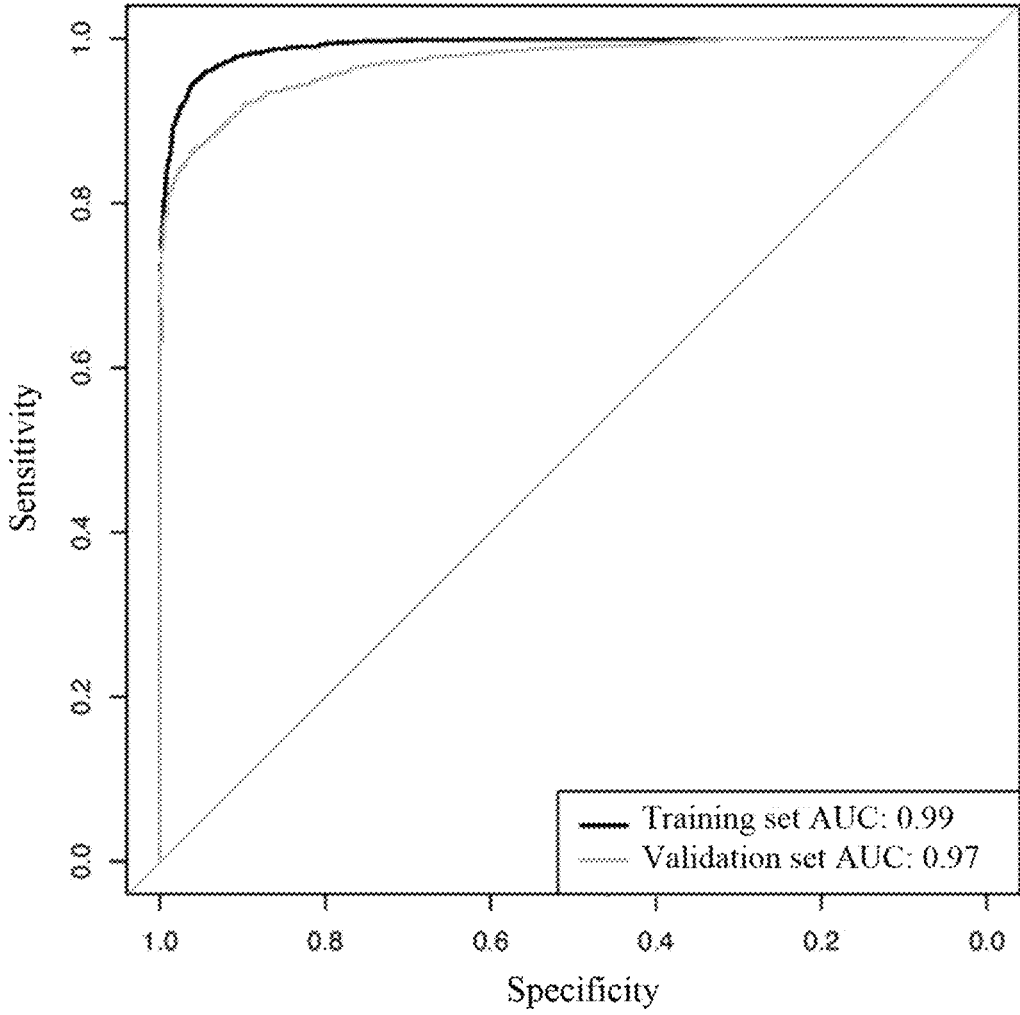
FIG. 4 shows the area under curve (AUC) performance of a multi-cancer early detection model in a training set and a validation set.
Figure 5:
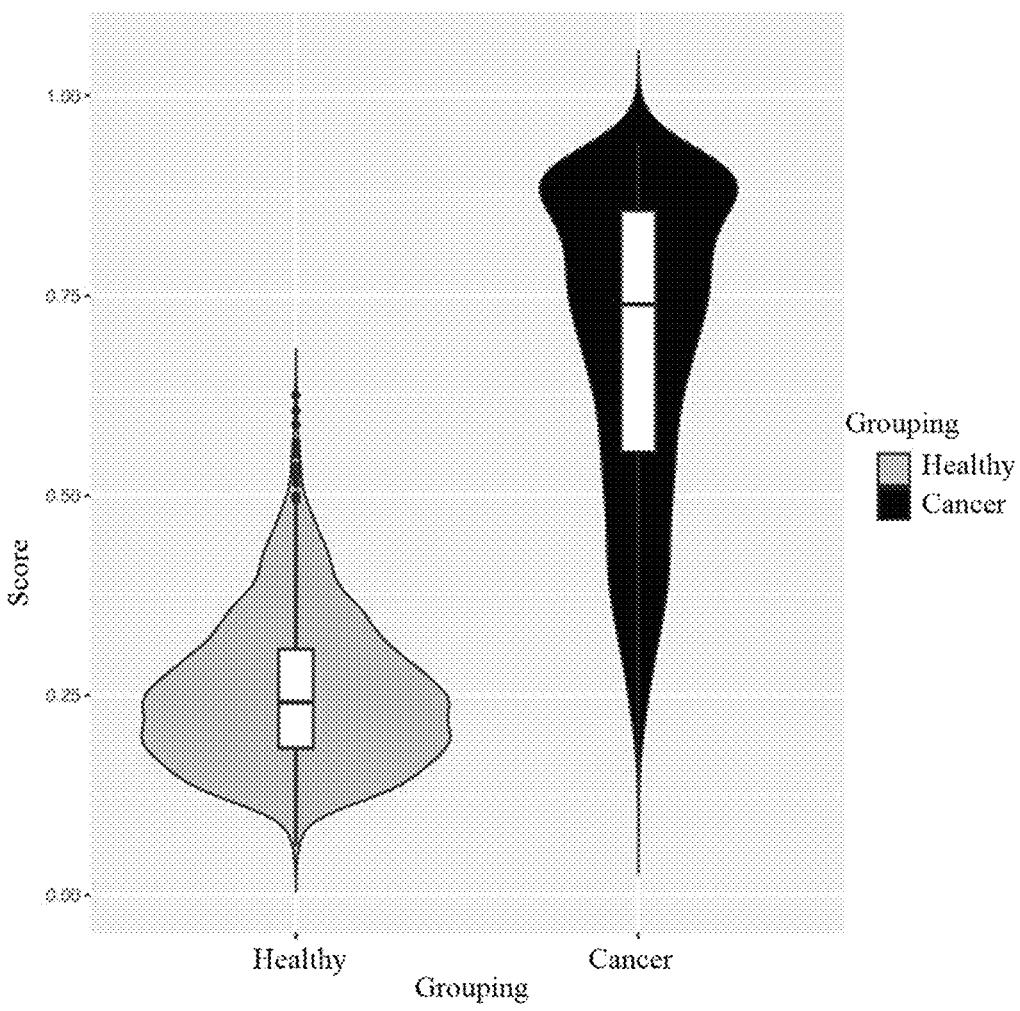
FIG. 5 shows a score distribution of a multi-cancer early detection model in a validation set.
Figure 6:
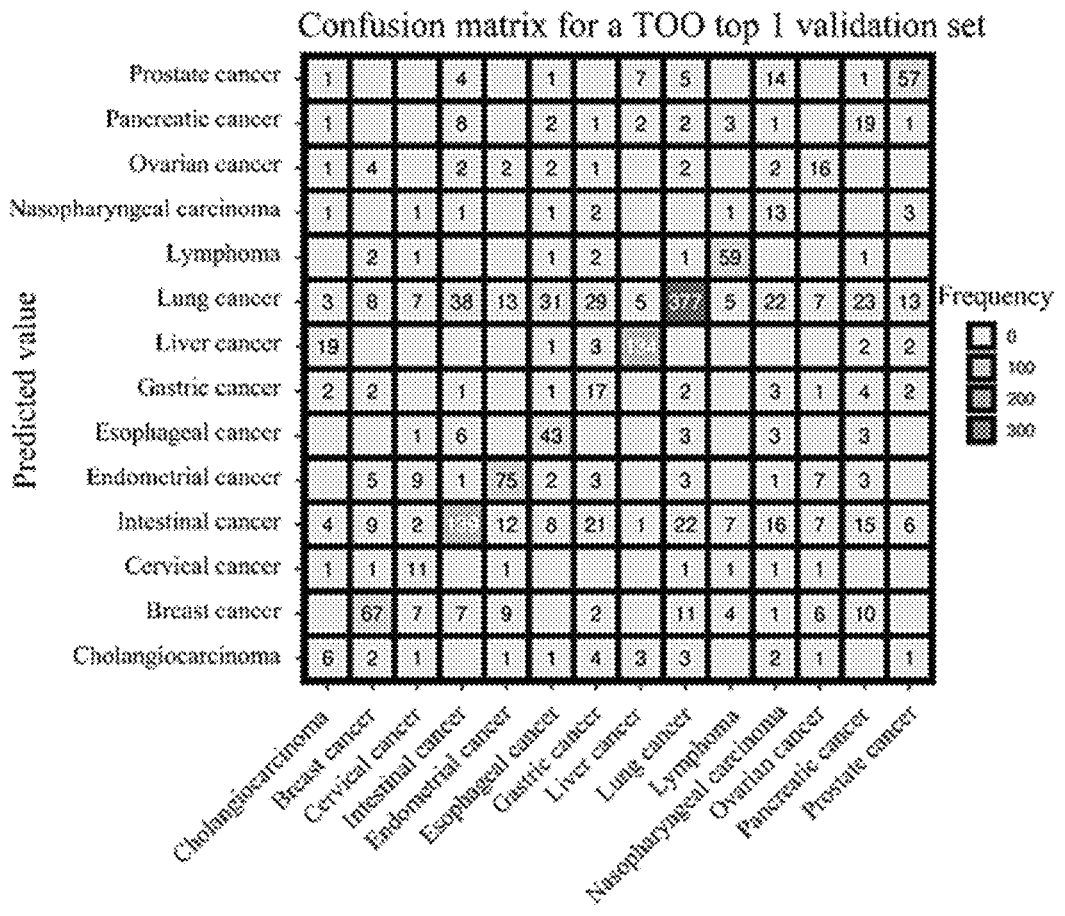
FIG. 6 shows a confusion matrix of detection results of a multi-cancer TOO model for top 1 cancers.
Figure 7:
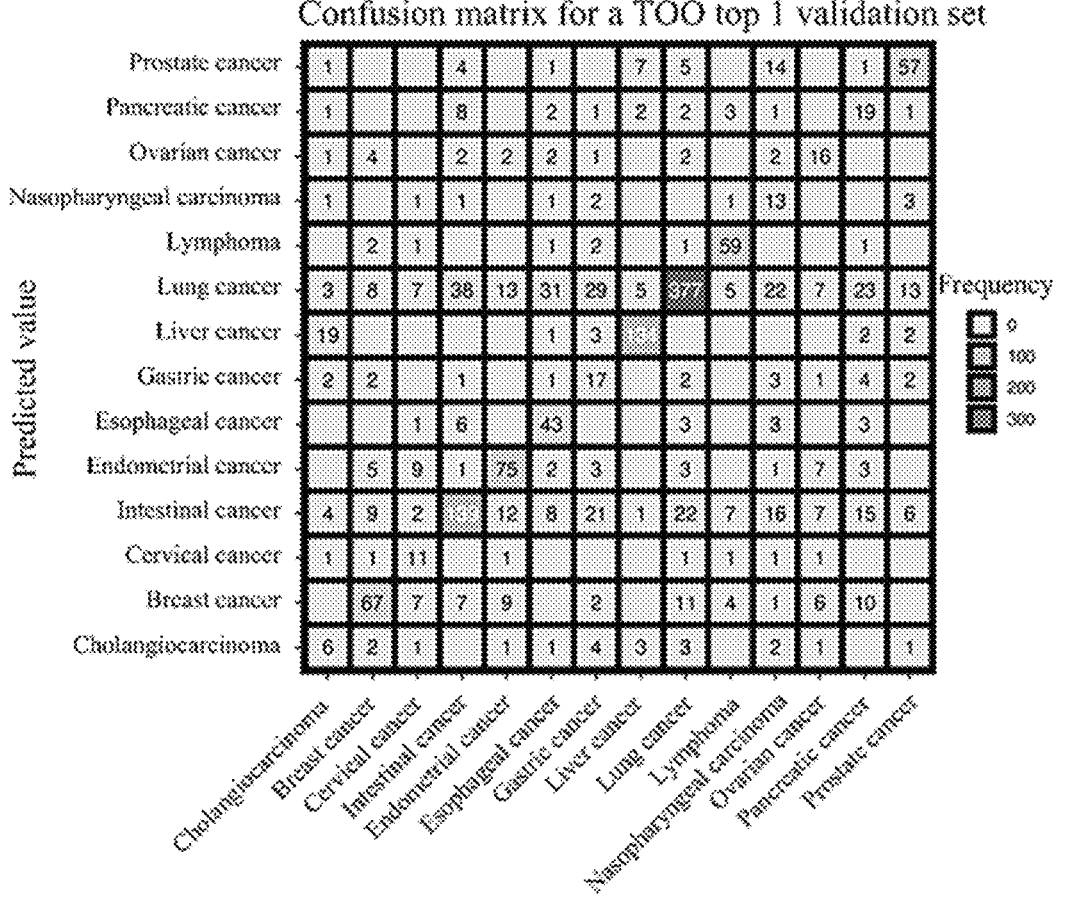
FIG. 7 shows a confusion matrix of detection results of a multi-cancer TOO model for top 2 cancers.
Figure 8:
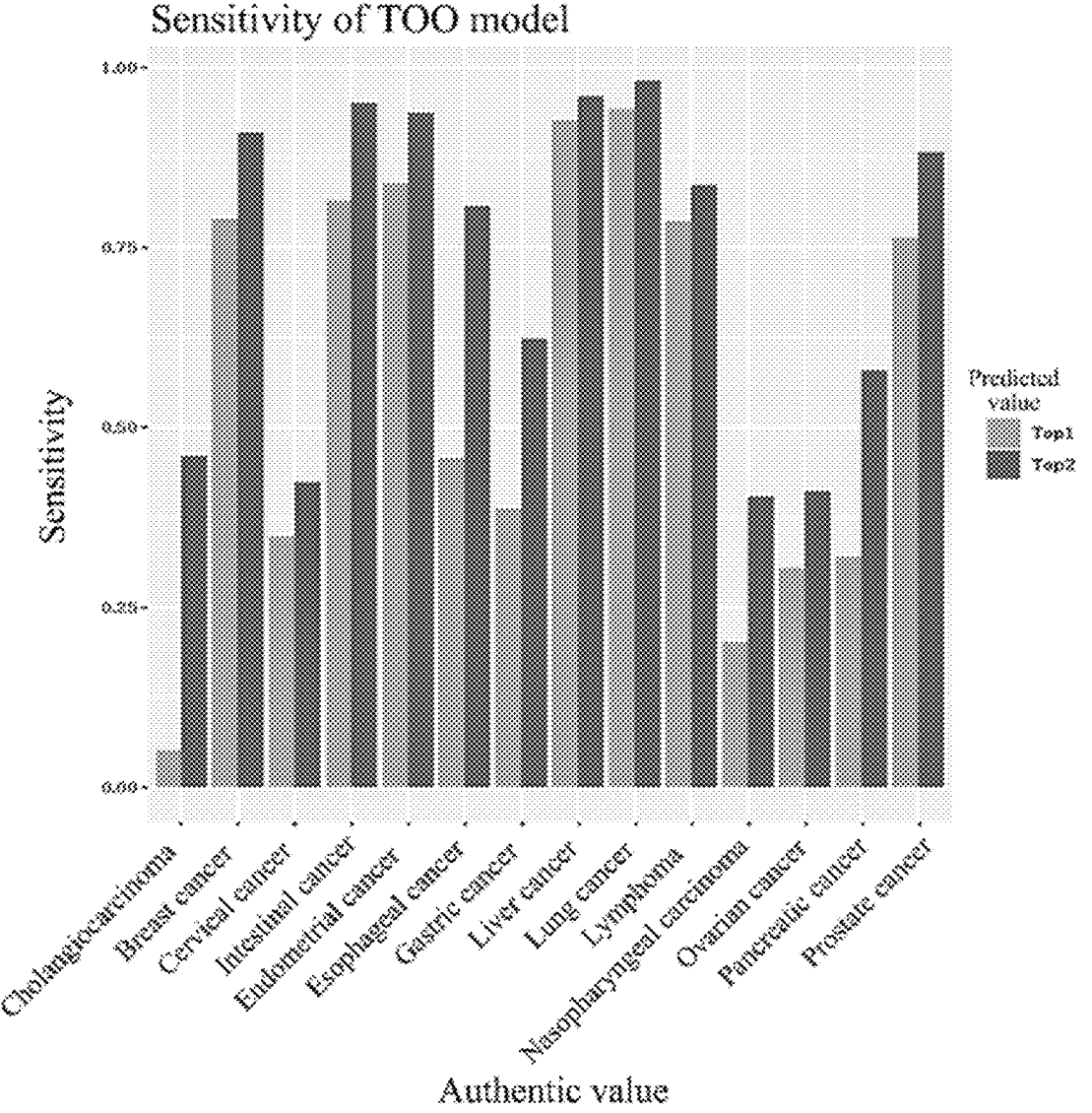
FIG. 8 shows the sensitivity performance of a multi-cancer TOO model in a validation set.

For sequencing results of low-coverage WGS (sequencing concentration: about 5×) for cfDNAs from 2,328 cancer patients (with one selected from the group consisting of cholangiocarcinoma, breast cancer, cervical cancer, intestinal cancer, endometrial cancer, esophageal cancer, gastric cancer, nasopharyngeal carcinoma, lung cancer, liver cancer, lymphoma, ovarian cancer, pancreatic cancer, and prostate cancer) and 2,553 healthy people, six eigenvalues as follows are analyzed: genome-wide FSC, FSD on long and short arms of chromosomes, 1 Mb-bin CNV, NP, FM, and MC/MS. A DL CNN is adopted to construct a multi-cancer early detection model, and five different algorithms are adopted to train a multi-cancer TOO model.

The present disclosure provides a multi-molecule, multi-feature, and multi-training algorithm diagnosis model based on high-throughput low-coverage WGS of plasma cfDNAs for the first time. In the present disclosure, a multi-cancer early detection model is constructed with CNN to screen and train a plurality of complicated feature gene markers. The model can diagnose 14 cancers at an early stage and trace a tissue of origin for these cancers, with characteristics such as non-invasiveness, low throughput, and high detection specificity and sensitivity. The performance of the model is validated with a validation set consisting of 1,633 cancer patients (suffering from one of the 14 cancers involved in the present disclosure) and 1,657 healthy people, and the validation set can still allow the high specificity and high sensitivity. A multi-cancer early detection model is constructed with samples of 1,633 patients and 1,657 healthy people, while a multi-cancer TOO model is constructed with samples of 1,633 patients.

In the present disclosure, steps such as extraction of cfDNAs from blood samples, library construction, and sequencing first need to be conducted. There is no special limitation on methods for the extraction and library construction here, and these methods can be obtained by adjusting the methods in the prior art. In a process of the sequencing here, the sequencing technology in the prior art can be adopted to acquire base information of cfDNAs. Data sets adopted for the model construction in the present disclosure are as follows:

The sample data included in the present disclosure are derived from data acquired by the applicants of the present disclosure in a detection work. The sample data of the training set and the validation set adopted in the present disclosure is totally derived from actual authentic clinical samples collected from a plurality of hospitals independently cooperated with the applicants of the present disclosure.

TABLE 2-continued

| | Cancer information for data sets | |
|---|---|---|
| Data set | Cancer type | Number of samples |
| | Lung cancer | 603 |
| | Ovarian cancer | 72 |
| | Pancreatic cancer | 126 |
| | Prostate cancer | 112 |
| | Cholangiocarcinoma | 55 |
| | Lymphoma | 125 |
| Validation set | Breast cancer | 100 |
| | Cervical cancer | 40 |
| | Intestinal cancer | 207 |
| | Endometrial cancer | 113 |
| | Esophageal cancer | 94 |
| | Gastric cancer | 85 |
| | Nasopharyngeal carcinoma | 79 |
| | Liver cancer | 152 |
| | Lung cancer | 432 |
| | Ovarian cancer | 46 |
| | Pancreatic cancer | 81 |
| | Prostate cancer | 85 |
| | Cholangiocarcinoma | 39 |
| | Lymphoma | 80 |

Extraction and sequencing methods for plasma cfDNA samples: 8 mL of a whole blood sample is collected from each patient by a purple blood collection tube (ethylenediaminetetraacetic acid (EDTA)-containing anticoagulant tube), then the purple blood collection tube is centrifuged in time (within 2 h) to isolate plasma, and the plasma is delivered to a laboratory and subjected to cfDNA extraction with a QIAGEN plasma DNA extraction kit. A library is constructed with the collected cfDNA samples, and then WGS is conducted on the collected cfDNA samples with a sequencing depth of about 5×. After the raw data is obtained, the raw data is aligned to a human reference genome to obtain base data information of corresponding reads.

The data of the present disclosure is processed mainly based on the following six molecular features:

1. DNA FSC

The DNA FSC reflects the feature of a coverage of a length of a cfDNA read. Machine learning is conducted with

TABLE 1

| | | | | | | | | | | | | Total number of people |
|---|---|---|---|---|---|---|---|---|---|---|---|---|
| | | | | | | | | | | | Unknown | |
| Data set | Group | Average age | Age distribution | Stage 0 | Stage I | Stage II | Stage III | Stage IV | Unknown stage | Female | Male | sex | |
| Training set | Cancer | 58 | 7-88 | 33 | 948 | 481 | 431 | 209 | 226 | 1141 | 1155 | 32 | 2328 |
| | Healthy | 57 | 21-89 | | | | \ | | | 1420 | 1121 | 12 | 2553 |
| Validation set | Cancer | 59 | 19-90 | 13 | 669 | 329 | 281 | 150 | 191 | 767 | 825 | 41 | 1633 |
| | Healthy | 57 | 23-85 | | | | \ | | | 930 | 724 | 3 | 1657 |

TABLE 2

| | Cancer information for data sets | |
|---|---|---|
| Data set | Cancer type | Number of samples |
| Training set | Breast cancer | 144 |
| | Cervical cancer | 63 |
| | Intestinal cancer | 260 |
| | Endometrial cancer | 180 |
| | Esophageal cancer | 144 |
| | Gastric cancer | 139 |
| | Nasopharyngeal carcinoma | 74 |
| | Liver cancer | 231 | a DNA fragment size ratio to build a prediction model, so as to distinguish between different cancers. Lengths of cfDNA reads of cancer patients (suffering from one of the 14 cancers involved in the present disclosure) are compared, and it is found that there is a difference between fragments of 100 bp to 150 bp and fragments of 151 bp to 220 bp in terms of the distribution on chromosomes, which can be adopted as a distinguishing feature.

The cfDNA read length data is obtained by the following method: In an aligned BAM file, the quality, length, and alignment position information of each read is recorded. The human reference genome is an hg19 sequence provided by the University of California, Santa Cruz (UCSC). The human reference genome is divided into 541 windows according to a length of 5 Mb. Quantities of short (100 bp to 150 bp) and long (151 bp to 220 bp) reads in each window are counted separately. According to statistical results for quantities of various reads in all windows, a quantity of each read is normalized as follows: normalized value=(original value-average value)/standard deviation. As a result, a data set of 1,082 (541×2) quantities of reads with different lengths is obtained.

2. DNA FSD

On the basis that the DNA FSC is obtained, in order to acquire high-resolution read results, 39 regions of long and short arms of each chromosome of the human reference genome are taken as windows, as shown in Table 3:

TABLE 3

| Position information of long and short arms of chromosomes | | | | | |
|---|---|---|---|---|---|
| chr1_p | chr4_q | chr8_p | chr11_q | chr16_q | chr20_p |
| chr1_q | chr5_p | chr8_q | chr12_p | chr17_p | chr20_q |
| chr2_p | chr5_q | chr9_p | chr12_q | chr17_q | chr21_q |
| chr2_q | chr6_p | chr9_q | chr13_q | chr18_p | chr22_q |
| chr3_p | chr6_q | chr10_p | chr14_q | chr18_q | |
| chr3_q | chr7_p | chr10_q | chr15_q | chr19_p | |
| chr4_p | chr7_q | chr11_p | chr16_p | chr19_q | |

A fragment of 100 bp to 220 bp is divided into 24 length gradients with an increment of 5 bp (such as 100 bp to 104 bp, 105 bp to 109 bp . . . on a 1q arm of chr1). Quantities of fragments of each length gradient in windows of short and long arms are counted and normalized to obtain a total of 936 feature results for high-resolution DNA FSD (936=39× 24 normalization results for the length gradients).

3. 1 Mb-Bin CNV

CNVs are highly correlated with individual cancers. Although it has been possible to distinguish between cancers by detecting some cancer-associated genes or CNVs in specific genomic intervals, there are still rare or unknown genes or intervals that can provide potential CNV information. Collection method: For WGS data of each sample to be tested, chromosomes 1 to 22 of the reference gene each are divided into windows without an overlap according to a length of 1 Mb. A read depth in each window is calculated for each sample by bedtools coverage, and corrected according to a GC content and an average alignment ability record (UCSC BigWig file) for each window to obtain individual read depth information of 2,475 windows. A CNV logarithm for each window is constructed with a hidden Markov model (HMM) and a control baseline depth of each window population, namely, log 2 (corrected and normalized depth for a sample to be tested/corrected and normalized depth for a population baseline), so as to obtain CNV information of each sample to be tested.

4. NP

Transcription factors are selected from GTRD (URL: gtrd.biouml.org/#!) (v21.12), and transcription factors without a known transcription site in a CIS-BP database (URL: cisbp.ccbr.utoronto.ca/) (v2.00) are excluded to obtain 854 transcription factors with more than 10,000 highly matched sites in total.

For the transcription factors obtained above, with a range from −5 kb to +5 kb near transcription sites in target transcription factors as a window, fragments with a length of 100 bp to 220 bp capable of being aligned to these windows are acquired. For these fragments, GC correction is conducted and a sequencing depth curve is smoothed by a Savitzky-Golay filter with a polynomial order of 3 to obtain a final profile curve of each transcription factor.

After the profile curve of each transcription factor is obtained, the following three features are extracted for each transcription factor (a total of 854×3=2,563 features are extracted):

1) For all transcription sites of each transcription factor, an average depth from 1 kb at an upper end to 1 kb at a lower end of each transcription site is calculated.

2) A central depth of each transcription factor is calculated.

3) Fast Fourier transform is conducted on the profile curve to obtain an amplitude value of a peak point of a nucleosome amplitude signal.

5. FM

A methylation pattern of cfDNA is inferred with FM of cfDNA. A CpG methylation status of a region can be inferred according to a cfDNA cleavage profile around CpG and two tandem CpG dinucleotide sites. Cleavage profiles associated with hypermethylated and hypomethylated CpG sites are compared, and it is found that a cleavage proportion of hypermethylated CpG sites (position 0) is twice a cleavage proportion of hypomethylated CpG sites. Therefore, the differential cleavage of a CpG site at positions 0 and 1 of cfDNA depends on a methylation status, which will eventually lead to the difference in a terminal motif. A CpG site in a methylation status tends to have more endpoints (the CGN motif) at position 0 (N can represent any nucleotide selected from the group consisting of A, C, G, and T) and less endpoints at position 1 (the NCG motif). Therefore, read proportions of NCG and CGN motifs (8 types, the read proportions each are obtained as follows: a proportion of reads at each site including a specific base segment in a depth of the site is calculated, and then an average proportion of the specific base segment at all sites is taken as a read proportion of the specific base segment) and a ratio of the read proportions (the ratio refers to a ratio of a total read proportion of all base segments of NCG to a total read proportion of all base segments of CGN) are counted for this feature.

In addition, the two tandem CpG dinucleotide sites are also high-frequency methylated regions. Therefore, in addition to a single CpG site, read proportions of broken endpoints C1.NCG (4 motifs), C1.CGN (4 motifs), C2.NCG (4 motifs), and C2.CGN (4 motifs) of the two tandem CpG dinucleotide sites, a C1.CGN/NCG motif ratio, and a C2.CGN/NCG motif ratio are also adopted as features of FM.

Therefore, a data composition of the fifth eigenvalue includes: 1) read proportions of NCG and CGN motifs at breaks in broken CpG sites and a ratio of the read proportions, and 2) read proportions of NCG and CGN motifs at breaks in each CpG of two tandem broken CpG dinucleotide sites and a ratio of the read proportions. In the 1), quantities of reads of NCG and CGN of all CpG sites and a ratio are calculated. In the 2), only quantities of NCG and CGN for each CpG site of adjacent sites CpGCpG and a ratio are calculated. A total of 27 ((4+4+1)×3) features are obtained.

6. MC/MS

The MC/MS includes the following two features for SBSs detected in WGS: MC and MS.

Mutation events occur throughout the life of somatic cells of an individual. Both endogenous processes and exogenous exposures may lead to different mutations in a genome of somatic cells. Because cfDNA fragments are released and enter a circulatory system during cell division, cfDNA fragments may reflect MS in somatic tissues. MC of a tumor is defined for SBS. Two-base mutations of the four bases of A, T, C, and G can be divided into the following six modes, C>A, C>G, C>T, T>A, T>C, and T>G. A context of a sequence where a mutation site is located is further considered, that is, bases taken from the upstream and the downstream respectively and a base of the mutation site constitute a tribase motif, with a total of 96 modes (4×4×6=96). A frequency distribution of reads in each mode after SNPs are removed is acquired to obtain the original 96 MCs. The frequency distribution in each mode is MC.

For the original reads with SNP not removed, frequency distributions in the above 96 modes are acquired similarly, and then transformed into MSs through NMF. The 96 MCs are factorized by NMF to obtain 79 MSs. Different MSs have different biological meanings, and each MS has respective 96 base mutation proportion distributions. The NMF here can be conducted through calculation of SigProfilerMatrixGeneratorR of an R package. During data processing, gene sequences undergoing mass pruning are aligned to the hg19 human reference genome, repeat reads are removed, sorting and indexing are conducted, and an average sequencing depth is calculated. In order to ensure an accuracy of analysis, reads with alternative alignments or with a length of more than 300 base pairs are excluded, and repeat regions or regions with low complexity are further shielded. A GC content is normalized by an LOESS smoothing method with 400 base pairs as a unit. The final MC/MS includes an MC portion and an MS portion.

The SNPs are removed for MC, and the SNPs are retained for MS. In order to further reduce the influence of a plurality of potential noise sources from a healthy population, a baseline control is constructed from a sample pool of 300 healthy individuals. According to the same process as above (including sequencing depth correction), 96 MCs are generated for each healthy control individual, and a mean of these 300 control samples is set as a baseline value for the MCs. The following two baseline controls are generated: a baseline with SNPs removed (for MC) and a baseline with SNPs retained (for MS).

Through the above data acquisition, the initial data vectors of these six types of data can be obtained. The six types of features are input into CNN to construct a multi-cancer early detection model. The multi-cancer early detection model can be used to distinguish cancer patients (14 cancers) from healthy people. Further, on this basis, the above six types of data are input into five different algorithms for integration to construct a multi-cancer TOO model. The multi-cancer TOO model can be further used in patients with known tumors to distinguish between tumors.

During the construction of the above two models, the following classification models are adopted:

CNN

CNN is a feedforward neural network that includes a convolution computation and has a deep structure. CNN is a representative algorithm of DL. CNN adopts a local connection and weight sharing, which can reduce a quantity of weights to make CNN easily optimized, reduce the complexity of a model, and reduce a risk of overfitting. Neurons in each layer of CNN are arranged in the following three dimensions: a width, a height, and a depth. A width and a height are usually determined by parameters associated with a convolution computation and a pooling operation. A depth refers to a number of channels of a feature, and is usually determined by a number of convolution kernels. CNN has the following three major layers: a convolutional layer, a pooling layer, and a fully-connected layer. In the convolutional layer, filters, as a small matrix, are applied to a specified region of a feature, and a dot product of an input eigenvector and a filter is calculated. The dot product is further provided for an output array. Then, the filters are allowed to move by a stride, and this process is repeated until a kernel scans the entire input eigenvector. After each convolution computation, a corresponding feature of CNN is transformed by a rectified linear unit (ReLU) to introduce a non-linear feature for a model. The pooling layer conducts a similar dimensionality reduction operation to the convolutional layer. A computation of the pooling layer causes the filters to scan the entire input eigenvector, but the filters do not have weights. Each node of the fully-connected layer is directly connected to a node in the next layer. The fully-connected layer generally serves as the last layer of CNN. The fully-connected layer conducts a classification task based on the features extracted by the previous layers and different filters. A softmax activation function is usually adopted to classify inputs, so as to produce a probability of 0 to 1.

GLM

GLM is an extension of a linear model, and establishes a mathematical relationship between a mathematical expectation of a response variable and a predictor variable of a linear combination through a link function. GLM is mainly characterized in that a natural metric of data is not forcibly changed. GLM is a common binary classification strategy.

GBM

GBM is a common algorithm in machine learning. A basic principle of GBM is as follows: according to negative gradient information of a loss function of the current model, a newly-added base classifier is trained, and then a trained base classifier is combined into the current model in an accumulative manner to obtain the optimal model. The GBM has advantages such as prominent training effect and uneasy overfitting.

RF

RF is a powerful classification and regression tool. When a group of data sets is provided, RF can randomly extract a part of information to generate a group of decision trees that help classification or regression, provide node splitting attributes, and continuously repeat the random extraction until splitting can no longer occur. A final prediction result is obtained by combining all splitting attribute results.

DL

DL is based on a multi-layer feedforward artificial neural network (ANN) that adopts backpropagation to allow training of stochastic gradient descent. The artificial neural network can include a large number of hidden layers, and these hidden layers each are composed of neurons with hyperbolic tangents, corrections, and maximal power activation functions. Advanced functions such as adaptive learning rate, rate annealing, momentum training, dropout, L1 or L2 regularization, checkpointing, and grid search can enable a high prediction accuracy. During learning and training, each compute node adopts multithreading (asynchronous) to train a copy of global model parameters on local data, and periodically contributes to a global model through model averaging on the network. Feedforward ANN models, also known as deep neural networks (DNNs) or multi-layer perceptrons (MLPs), are the most common type of DNNs. A main principle is as follows: a plurality of perceptrons of a plurality of inputs and outputs can select appropriate input and output layers through the design and establishment of an appropriate number of neuron compute nodes and multi-layer operation hierarchies, and establish a functional relationship from inputs to outputs through network learning and optimization, which can be as close as possible to an actual association relationship.

XGBoost

XGBoost is an efficient open-source implementation of GBM. Compared with the traditional GBM, XGBoost introduces parallelization, and thus has a high speed. XGBoost introduces a second-order approximation for an objective function to obtain an analytical solution, and the analytical solution is used to establish a decision tree, such that the objective function is optimal. XGBoost introduces a regular term portion, which can control the complexity of a model to prevent overfitting. XGBoost introduces feature subsampling similar to RF, which can reduce both overfitting and computations.

In a modeling process, according to the existing parameter optimization mode, a random grid search parameter algorithm can also be adopted to optimize a model. Random search is a common method of hyperparameter optimization for machine learning. Random search is as follows: parameter values are randomly selected from a specific model parameter range, and the optimal parameter combination is selected from a plurality of selected parameter values. The method does not try all possible combinations, but adopts a random combination of a specified quantity of random values for each hyperparameter. Compared with the model parameter adjustment through manual optimization and network search, random search can allow a prominent effect with few searching times to provide an efficient solution (especially when there is a large number of parameters).

A framework for constructing a multi-cancer early detection model is as follows:

The multi-cancer early detection model mainly includes CNN and stacking. In the multi-cancer early detection model, characteristics of each feature are collected by conducting 2nd-level meta-learning for a 1st-level base model of a plurality of features to find the optimal integration approach.

An architecture of the CNN model is as follows:

An input layer configured to receive input eigenvectors.

Three convolutional layers, where each of the three convolutional layers conducts feature extraction through a convolution kernel.

Three fully-connected layers, which are responsible for high-level synthesis and classification of features.

An output layer configured to output a probability of a sample to have a cancer.

Input of the eigenvectors:

The first, second, third, fourth, fifth, and sixth features are input as eigenvectors directly into the input layer of the model.

A convolutional layer processing flow in the convolutional layers is as follows:

In the convolutional layers, the eigenvectors are first processed by a convolution kernel. Then, the nonlinearity is introduced with a ReLU activation function to enhance an expressive ability of the model. Then, batch normalization is conducted to increase a training speed and improve the stability of the model. Finally, a max pooling operation is applied to reduce a computing quantity and extract key features.

A processing flow of the fully-connected layers is as follows:

Eigenvectors processed by the convolutional layers are further activated by ReLU. Then, activated eigenvectors pass through the three fully-connected layers consecutively. These fully-connected layers are responsible for synthesis and classification of features.

A function of the output layer is as follows: a predicted value is obtained through the output layer to indicate a probability of a sample to have a cancer.

The first, second, third, fourth, fifth, and sixth gene marker eigenvectors are input into the CNN to obtain convolutional base models of the six features, and stacking is conducted for results of these feature models to obtain final output results.

The importance of input features is predicted based on the analysis of a gradient of an output of a CNN model of the multi-cancer early detection model relative to an input (which is essentially a change rate of an output of a function relative to an input). The importance of the six features to the model is analyzed, and eigenvalues are simplified. Eigenvalues with top contributions in each feature set are selected as input vectors for the final model. The specific performance of each feature is shown in Table 4 (variables with top importance are selected for each feature):

TABLE 4

| | Important feature variables for CNV | |
|---|---|---|
| No. | Feature variable | Feature importance |
| 1 | CNV.8.95000001.96000000 | 4.699478149 |
| 2 | CNV.8.96000001.97000000 | 4.235770226 |
| 3 | CNV.15.76000001.77000000 | 3.591619015 |
| 4 | CNV.4.166000001.167000000 | 3.464466572 |
| 5 | CNV.4.188000001.189000000 | 3.272450686 |
| 6 | CNV.12.38000001.39000000 | 3.107181311 |
| 7 | CNV.4.169000001.170000000 | 3.102098227 |
| 8 | CNV.15.74000001.75000000 | 3.006942034 |
| 9 | CNV.1.241000001.242000000 | 2.998541117 |
| 10 | CNV.15.77000001.78000000 | 2.920005083 |
| 11 | CNV.5.137000001.138000000 | 2.886130095 |
| 12 | CNV.8.100000001.101000000 | 2.859395742 |
| 13 | CNV.4.168000001.169000000 | 2.834031582 |
| 14 | CNV.4.167000001.168000000 | 2.789381742 |
| 15 | CNV.8.92000001.93000000 | 2.763691902 |
| 16 | CNV.17.40000001.41000000 | 2.666691065 |
| 17 | CNV.8.98000001.99000000 | 2.604869604 |
| 18 | CNV.1.246000001.247000000 | 2.591870308 |
| 19 | CNV.12.31000001.32000000 | 2.590196609 |
| 20 | CNV.11.7000001.8000000 | 2.573495388 |
| 21 | CNV.1.244000001.245000000 | 2.523672104 |
| 22 | CNV.4.189000001.190000000 | 2.483618021 |
| 23 | CNV.5.2000001.3000000 | 2.467456818 |
| 24 | CNV.3.71000001.72000000 | 2.451675892 |
| 25 | CNV.2.113000001.114000000 | 2.444600344 |
| 26 | CNV.8.137000001.138000000 | 2.43024683 |
| 27 | CNV.4.186000001.187000000 | 2.401911974 |
| 28 | CNV.7.150000001.151000000 | 2.367861748 |
| 29 | CNV.15.75000001.76000000 | 2.360578537 |
| 30 | CNV.3.69000001.70000000 | 2.35032773 |

TABLE 5

| | Important feature variables for DNA FSC | |
|---|---|---|
| No. | Feature variable | Feature importance |
| 1 | FSC.longA467 | 12.10260582 |
| 2 | FSC.longA147 | 11.91520786 |
| 3 | FSC.longA145 | 11.6095314 |
| 4 | FSC.longA43 | 10.46909332 |
| 5 | FSC.longA463 | 9.872754097 |
| 6 | FSC.longA129 | 9.018865585 |
| 7 | FSC.longA299 | 8.379597664 |
| 8 | FSC.longA253 | 8.110090256 |
| 9 | FSC.longA141 | 7.537289143 |
| 10 | FSC.longA469 | 7.525841236 |
| 11 | FSC.longA335 | 7.24737978 |
| 12 | FSC.longA401 | 7.107270241 |
| 13 | FSC.longA11 | 6.728011131 |

TABLE 5-continued

Important feature variables for DNA FSC

| No. | Feature variable | Feature importance |
|-----|------------------|--------------------|
| 14 | FSC.longA285 | 6.623027325 |
| 15 | FSC.longA403 | 6.56946373 |
| 16 | FSC.longA451 | 6.451249123 |
| 17 | FSC.longA282 | 6.412755489 |
| 18 | FSC.longA39 | 6.402050018 |
| 19 | FSC.longA143 | 6.330185413 |
| 20 | FSC.longA404 | 6.180294514 |
| 21 | FSC.longA182 | 6.15078783 |
| 22 | FSC.longA89 | 6.126684189 |
| 23 | FSC.longA475 | 5.985833168 |
| 24 | FSC.longA399 | 5.937766552 |
| 25 | FSC.longA495 | 5.835074425 |
| 26 | FSC.longA65 | 5.676570892 |
| 27 | FSC.longA298 | 5.498690605 |
| 28 | FSC.longA326 | 5.470083714 |
| 29 | FSC.longA402 | 5.4596138 |
| 30 | FSC.shortA461 | 5.394837856 |

In Table 5, a number after a name indicates a sequential number of a window, long indicates a long read, and short indicates a short read.

TABLE 6

Important feature variables for DNA FSD

| No. | Feature variable | Feature importance |
|-----|------------------|--------------------|
| 1 | FSD.chr18.18q.frag.205.209 | 20.42121506 |
| 2 | FSD.chr19.19q.frag.205.209 | 17.53946686 |
| 3 | FSD.chr4.4p.frag.105.109 | 16.25907516 |
| 4 | FSD.chr5.5p.frag.140.144 | 15.44139004 |
| 5 | FSD.chr12.12p.frag.120.124 | 15.00565529 |
| 6 | FSD.chr1.1q.frag.105.109 | 14.80774498 |
| 7 | FSD.chr12.12p.frag.115.119 | 14.73165417 |
| 8 | FSD.chr10.10q.frag.120.124 | 13.72606564 |
| 9 | FSD.chr2.2p.frag.195.199 | 13.4607563 |
| 10 | FSD.chr16.16p.frag.120.124 | 13.37007332 |
| 11 | FSD.chr16.16p.frag.100.104 | 13.29316998 |
| 12 | FSD.chr17.17p.frag.100.104 | 13.20422459 |
| 13 | FSD.chr17.17p.frag.205.209 | 12.72639465 |
| 14 | FSD.chr21.21q.frag.125.129 | 12.40562439 |
| 15 | FSD.chr22.22q.frag.130.134 | 11.81911182 |
| 16 | FSD.chr7.7q.frag.205.209 | 11.43208408 |
| 17 | FSD.chr20.20q.frag.130.134 | 11.36607552 |
| 18 | FSD.chr19.19q.frag.210.214 | 11.34836006 |
| 19 | FSD.chr12.12q.frag.120.124 | 11.30405998 |
| 20 | FSD.chr18.18p.frag.145.149 | 10.93693638 |
| 21 | FSD.chr18.18p.frag.135.139 | 10.64348602 |
| 22 | FSD.chr22.22q.frag.145.149 | 10.58805943 |
| 23 | FSD.chr20.20q.frag.110.114 | 10.54708767 |
| 24 | FSD.chr16.16q.frag.205.209 | 10.11178303 |
| 25 | FSD.chr3.3q.frag.105.109 | 9.826384544 |
| 26 | FSD.chr19.19p.frag.145.149 | 9.730751038 |
| 27 | FSD.chr15.15q.frag.120.124 | 9.713457108 |
| 28 | FSD.chr3.3q.frag.140.144 | 9.713056564 |
| 29 | FSD.chr11.11q.frag.115.119 | 9.660514832 |
| 30 | FSD.chr3.3p.frag.105.109 | 9.631393433 |

In Table 6, a number after Frag. indicates a distribution starting value of a length gradient.

TABLE 7

Important feature variables for FM

| No. | Feature variable | Feature importance |
|-----|------------------|--------------------|
| 1 | FM.TCG | 69.37298584 |
| 2 | FM.CG1.TCG | 49.82826996 |
| 3 | FM.ACG | 34.56561661 |
| 4 | FM.CG1.ACG | 22.34730911 |

TABLE 7-continued

Important feature variables for FM

| No. | Feature variable | Feature importance |
|-----|------------------|--------------------|
| 5 | FM.CGA | 21.04551888 |
| 6 | FM.CG1.GCG | 19.57393265 |
| 7 | FM.CG1.CCG | 18.32042885 |
| 8 | FM.CG2.CGT | 16.23113632 |
| 9 | FM.CG2.CGA | 16.21441269 |
| 10 | FM.CGC | 15.99518585 |
| 11 | FM.CCG | 14.81142902 |
| 12 | FM.CG2.CGC | 12.70541668 |
| 13 | FM.GCG | 11.03264904 |
| 14 | FM.CGT | 8.438772202 |
| 15 | FM.CG1.CGN_NCG_ratio | 5.75705862 |
| 16 | FM.CG2.CGG | 5.723210335 |
| 17 | FM.CG2.GCG | 3.807393551 |
| 18 | FM.CGG | 2.402243376 |
| 19 | FM.CG1.CGC | 2.229426622 |
| 20 | FM.CGN_NCG_ratio | 1.868193746 |
| 21 | FM.CG2.CGN_NCG_ratio | 0.654803693 |

TABLE 8

Important feature variables for NP

| No. | Feature variable | Feature importance |
|-----|------------------|--------------------|
| 1 | NP.854.central.SPI1 | 3.016494274 |
| 2 | NP.854.central.SP5 | 2.205516338 |
| 3 | NP.854.central.SP7 | 1.683006883 |
| 4 | NP.854.central.SP3 | 1.423332095 |
| 5 | NP.854.mean.ZNF544 | 1.034175873 |
| 6 | NP.854.central.CLOCK | 1.014402628 |
| 7 | NP.854.central.ZNF34 | 0.979273438 |
| 8 | NP.854.central.CXXC1 | 0.929762304 |
| 9 | NP.854.central.STAT5A | 0.877071798 |
| 10 | NP.854.central.CHAMP1 | 0.850279331 |
| 11 | NP.854.mean.NFYA | 0.83978945 |
| 12 | NP.854.central.ZNF555 | 0.787700593 |
| 13 | NP.854.mean.ZNF586 | 0.770612836 |
| 14 | NP.854.central.PRDM12 | 0.761878073 |
| 15 | NP.854.central.DACH1 | 0.740066648 |
| 16 | NP.854.mean.ZKSCAN1 | 0.724704325 |
| 17 | NP.854.central.ZNF394 | 0.719309986 |
| 18 | NP.854.central.CREM | 0.689140677 |
| 19 | NP.854.central.PPARG | 0.677028596 |
| 20 | NP.854.mean.ZNF530 | 0.668816447 |
| 21 | NP.854.mean.ATF5 | 0.643081009 |
| 22 | NP.854.central.STAT4 | 0.639900029 |
| 23 | NP.854.mean.ZNF581 | 0.634269059 |
| 24 | NP.854.central.CTCFL | 0.632130682 |
| 25 | NP.854.central.ATF1 | 0.627979815 |
| 26 | NP.854.central.ZNF292 | 0.600466192 |
| 27 | NP.854.mean.ZNF529 | 0.600425363 |
| 28 | NP.854.central.NFYB | 0.579684198 |
| 29 | NP.854.central.SPIB | 0.574260294 |
| 30 | NP.854.central.CUX1 | 0.567690909 |

In Table 8, central indicates an average depth, mean indicates a central depth, 854 indicates that 854 transcription factors are counted in total, and the last letter string indicates a name of a transcription factor.

TABLE 9

Important feature variables for MC/MS

| No. | Feature variable | Feature importance |
|-----|------------------|--------------------|
| 1 | MCMS.SBS10d | 0.003488905 |
| 2 | MCMS.SBS13 | 0.003299461 |
| 3 | MCMS.SBS11 | 0.002773776 |
| 4 | MCMS.SBS12 | 0.001778645 |
| 5 | MCMS.SBS10c | 0.001741777 |

TABLE 9-continued

| | Important feature variables for MC/MS | |
|---|---|---|
| No. | Feature variable | Feature importance |
| 6 | MCMS.GCGA | 0.001652474 |
| 7 | MCMS.SBS14 | 0.001633167 |
| 8 | MCMS.TCAC | 0.001487821 |
| 9 | MCMS.GCGT | 0.001408142 |
| 10 | MCMS.GCAC | 0.001255044 |
| 11 | MCMS.CTCT | 0.001177291 |
| 12 | MCMS.CTCG | 0.001149618 |
| 13 | MCMS.SBS6 | 0.001066531 |
| 14 | MCMS.CTGC | 0.001052176 |
| 15 | MCMS.ATCA | 0.000961088 |
| 16 | MCMS.GCTC | 0.000847113 |
| 17 | MCMS.GCAT | 0.000822444 |
| 18 | MCMS.ATAT | 0.000756263 |
| 19 | MCMS.GTAT | 0.000735576 |
| 20 | MCMS.CCGC | 0.000719685 |
| 21 | MCMS.SBS35 | 0.000689728 |
| 22 | MCMS.SBS1 | 0.000679269 |
| 23 | MCMS.SBS16 | 0.000678316 |
| 24 | MCMS.GCAG | 0.000674899 |
| 25 | MCMS.SBS37 | 0.000647716 |
| 26 | MCMS.GTCT | 0.000616975 |
| 27 | MCMS.SBS39 | 0.000611259 |
| 28 | MCMS.SBS27 | 0.000589941 |
| 29 | MCMS.CTGG | 0.000580379 |
| 30 | MCMS.CTAT | 0.00056757 |

A framework for constructing a multi-cancer TOO model is as follows:

A sample predicted as positive by the multi-cancer early detection model is subjected to cancer TOO prediction with the multi-cancer TOO model. The six gene marker features are also used as input features for the multi-cancer TOO model. All features adopt the five algorithms of GLM, GBM, RF, DL, and XGBoost. The hyperparameters and structures of random search are changed to allow sub-model training for each feature. All sub-models are screened by mean squared error (MSE). 3 optimal sub-models are selected for each gene marker feature, that is, 18 optimal sub-models (3×6=18 models) are finally selected. Eigenvalues are simplified, and eigenvalues with top contributions in each feature set are selected as input vectors for the final sub-models. In order to further improve the prediction performance of a classifier, stacking is conducted for the plurality of optimal sub-models trained and selected above. Stacking is an ensemble learning technology. In this technology, characteristics of each 1st-level classifier are collected by conducting 2nd-level meta-learning for a plurality of 1st-level base models to find the optimal integration approach, thereby improving the prediction performance of the model. A training algorithm adopted for the stacking in the present disclosure is GLM, which establishes a relationship between a mathematical expectation of a response variable and a predictor variable of a linear combination through a link function. The multi-cancer TOO model is a multi-classification model, and an output value of the multi-cancer TOO model is a probability of developing a cancer (the multi-cancer TOO model can predict a probability of a sample to be tested to have the 14 cancers such as cholangiocarcinoma, intestinal cancer, and lung cancer involved in the present disclosure, and the maximum values (Top1) and the second maximum values (Top2) among prediction results of the 14 cancers are taken as the final determination results). Feature variables with top contributions of the optimal models selected for each feature and corresponding contributions are shown in Table 10.

TABLE 10

| | Important feature variables for CNV | |
|---|---|---|
| No. | Feature variable | Contribution |
| 1 | CNV.2.164000001.165000000 | 0.563914551 |
| 2 | CNV.16.2000001.3000000 | 0.414551016 |
| 3 | CNV.19.3000001.4000000 | 0.369360789 |
| 4 | CNV.11.2000001.3000000 | 0.346061828 |
| 5 | CNV.21.45000001.46000000 | 0.342110401 |
| 6 | CNV.11.61000001.62000000 | 0.331314771 |
| 7 | CNV.16.71000001.72000000 | 0.305743739 |
| 8 | CNV.7.1000001.2000000 | 0.303962384 |
| 9 | CNV.19.2000001.3000000 | 0.303391398 |
| 10 | CNV.10.134000001.135000000 | 0.299882301 |
| 11 | CNV.1.12000001.13000000 | 0.299189032 |
| 12 | CNV.9.136000001.137000000 | 0.299156384 |
| 13 | CNV.16.85000001.86000000 | 0.288105458 |
| 14 | CNV.2.78000001.79000000 | 0.284695229 |
| 15 | CNV.10.24000001.25000000 | 0.284277132 |
| 16 | CNV.13.113000001.114000000 | 0.282174506 |
| 17 | CNV.9.115000001.116000000 | 0.282086557 |
| 18 | CNV.5.178000001.179000000 | 0.281827531 |
| 19 | CNV.11.90000001.91000000 | 0.279297822 |
| 20 | CNV.17.43000001.44000000 | 0.278570571 |
| 21 | CNV.19.4000001.5000000 | 0.276371555 |
| 22 | CNV.14.44000001.45000000 | 0.275901016 |
| 23 | CNV.14.41000001.42000000 | 0.274095046 |
| 24 | CNV.22.47000001.48000000 | 0.270514991 |
| 25 | CNV.17.35000001.36000000 | 0.268422385 |
| 26 | CNV.22.43000001.44000000 | 0.267937742 |
| 27 | CNV.7.41000001.42000000 | 0.261147969 |
| 28 | CNV.17.80000001.81000000 | 0.26081646 |
| 29 | CNV.2.104000001.105000000 | 0.259432997 |
| 30 | CNV.9.135000001.136000000 | 0.256940402 |

TABLE 11

| | Important feature variables for DNA FSC | |
|---|---|---|
| No. | Feature variable | Contribution |
| 1 | FSC.longA503 | 0.300436615 |
| 2 | FSC.longA92 | 0.277248857 |
| 3 | FSC.longA269 | 0.263397187 |
| 4 | FSC.longA89 | 0.256332797 |
| 5 | FSC.longA461 | 0.255161679 |
| 6 | FSC.longA403 | 0.244145111 |
| 7 | FSC.longA383 | 0.238186341 |
| 8 | FSC.longA3 | 0.237984719 |
| 9 | FSC.longA481 | 0.237340931 |
| 10 | FSC.longA422 | 0.235416913 |
| 11 | FSC.longA77 | 0.228167574 |
| 12 | FSC.longA75 | 0.227733944 |
| 13 | FSC.longA391 | 0.227407204 |
| 14 | FSC.longA253 | 0.224129376 |
| 15 | FSC.longA325 | 0.222809592 |
| 16 | FSC.longA475 | 0.222441618 |
| 17 | FSC.longA59 | 0.22111174 |
| 18 | FSC.longA528 | 0.219582637 |
| 19 | FSC.longA149 | 0.219394836 |
| 20 | FSC.longA4 | 0.217967655 |
| 21 | FSC.longA393 | 0.21675002 |
| 22 | FSC.longA204 | 0.216678556 |
| 23 | FSC.longA510 | 0.216164172 |
| 24 | FSC.longA477 | 0.215054459 |
| 25 | FSC.longA398 | 0.212552554 |
| 26 | FSC.longA536 | 0.212343602 |
| 27 | FSC.longA506 | 0.210727291 |
| 28 | FSC.longA349 | 0.208441771 |
| 29 | FSC.longA472 | 0.208063126 |
| 30 | FSC.longA389 | 0.206506417 |

TABLE 12

| | Important feature variables for DNA FSD | |
| No. | Feature variable | Contribution |
| --- | --- | --- |
| 1 | FSD.chr1.1p.FSC.170.174 | 0.191009838 |
| 2 | FSD.chr10.10p.FSC.170.174 | 0.185686318 |
| 3 | FSD.chr8.8p.FSC.160.164 | 0.179577858 |
| 4 | FSD.chr13.13q.FSC.170.174 | 0.178880089 |
| 5 | FSD.chr4.4p.FSC.165.169 | 0.172977313 |
| 6 | FSD.chr3.3p.FSC.165.169 | 0.172811394 |
| 7 | FSD.chr6.6q.FSC.170.174 | 0.171492263 |
| 8 | FSD.chr22.22q.FSC.170.174 | 0.170975063 |
| 9 | FSD.chr17.17q.FSC.170.174 | 0.166271002 |
| 10 | FSD.chr3.3p.FSC.170.174 | 0.165209984 |
| 11 | FSD.chr10.10p.FSC.155.159 | 0.161065132 |
| 12 | FSD.chr17.17q.FSC.155.159 | 0.160815399 |
| 13 | FSD.chr19.19q.FSC.170.174 | 0.158523515 |
| 14 | FSD.chr3.3p.FSC.160.164 | 0.158121871 |
| 15 | FSD.chr9.9q.FSC.170.174 | 0.157148721 |
| 16 | FSD.chr16.16p.FSC.175.179 | 0.155217785 |
| 17 | FSD.chr6.6p.FSC.170.174 | 0.154940871 |
| 18 | FSD.chr21.21q.FSC.170.174 | 0.15447461 |
| 19 | FSD.chr13.13q.FSC.160.164 | 0.154073569 |
| 20 | FSD.chr1.1p.FSC.155.159 | 0.152025379 |
| 21 | FSD.chr13.13q.FSC.155.159 | 0.151753463 |
| 22 | FSD.chr6.6q.FSC.155.159 | 0.15076443 |
| 23 | FSD.chr4.4p.FSC.170.174 | 0.150163525 |
| 24 | FSD.chr19.19p.FSC.170.174 | 0.149912025 |
| 25 | FSD.chr1.1q.FSC.160.164 | 0.149282091 |
| 26 | FSD.chr13.13q.FSC.145.149 | 0.148952692 |
| 27 | FSD.chr6.6q.FSC.165.169 | 0.14888487 |
| 28 | FSD.chr6.6q.FSC.160.164 | 0.148820992 |
| 29 | FSD.chr19.19q.FSC.160.164 | 0.147806448 |
| 30 | FSD.chr1.1q.FSC.170.174 | 0.147605366 |

TABLE 13

| | Important feature variables for FM | |
| No. | Feature variable | Contribution |
| --- | --- | --- |
| 1 | FM.CGC | 1 |
| 2 | FM.CG1.TCG | 0.951173897 |
| 3 | FM.CGT | 0.910333761 |
| 4 | FM.CG1.CGC | 0.842915063 |
| 5 | FM.CG1.CCG | 0.828424069 |
| 6 | FM.CGG | 0.784889708 |
| 7 | FM.CGA | 0.784398725 |
| 8 | FM.CGN__NCG__ratio | 0.766806487 |
| 9 | FM.CCG | 0.698450938 |
| 10 | FM.CG2.CGG | 0.648684796 |
| 11 | FM.CG1.GCG | 0.641369813 |
| 12 | FM.CG2.CGT | 0.624322279 |
| 13 | FM.CG2.CGA | 0.6053874 |
| 14 | FM.ACG | 0.585612547 |
| 15 | FM.CG2.CGC | 0.573554048 |
| 16 | FM.CG1.ACG | 0.535710117 |
| 17 | FM.GCG | 0.526621717 |
| 18 | FM.CG2.GCG | 0.493788791 |
| 19 | FM.TCG | 0.455359265 |
| 20 | FM.CG1.CGN__NCG__ratio | 0.268664483 |
| 21 | FM.CG2.CGN__NCG__ratio | 0.138869747 |

TABLE 14

| | Important feature variables for NP | |
| No. | Feature variable | Contribution |
| --- | --- | --- |
| 1 | NP.854.central.ZSCAN4 | 0.728803611 |
| 2 | NP.854.central.ZSCAN16 | 0.699687537 |
| 3 | NP.854.central.FOXN3 | 0.602607379 |
| 4 | NP.854.central.HMGA1 | 0.448861198 |
| 5 | NP.854.central.ZNF384 | 0.396545034 |
| 6 | NP.854.mean.ZSCAN4 | 0.334841857 |

TABLE 14-continued

| | Important feature variables for NP | |
| No. | Feature variable | Contribution |
| --- | --- | --- |
| 7 | NP.854.mean.ZSCAN16 | 0.328033821 |
| 8 | NP.854.mean.FOXN3 | 0.310202811 |
| 9 | NP.854.central.ZNF362 | 0.306811994 |
| 10 | NP.854.mean.MBD2 | 0.287812274 |
| 11 | NP.854.amplitude.NFIB | 0.273995052 |
| 12 | NP.854.central.ZNF512 | 0.230432421 |
| 13 | NP.854.mean.BACH2 | 0.224400365 |
| 14 | NP.OCF__Tcell | 0.217227681 |
| 15 | NP.854.amplitude.FOSL1 | 0.198505448 |
| 16 | NP.854.central.ZNF518A | 0.173784653 |
| 17 | NP.854.central.DACH1 | 0.172795275 |
| 18 | NP.854.mean.HMGA1 | 0.163896579 |
| 19 | NP.854.amplitude.ZBTB2 | 0.161452377 |
| 20 | NP.854.mean.ZNF597 | 0.156218511 |
| 21 | NP.854.mean.CDC5L | 0.143641505 |
| 22 | NP.854.central.PHOX2B | 0.141109424 |
| 23 | NP.854.central.MBD2 | 0.117981199 |
| 24 | NP.854.central.E2F6 | 0.113902404 |
| 25 | NP.854.central.TRPS1 | 0.111194847 |
| 26 | NP.854.central.PAX8 | 0.110097879 |
| 27 | NP.854.central.SP140 | 0.104149768 |
| 28 | NP.854.central.ZNF121 | 0.100393642 |
| 29 | NP.854.central.CDC5L | 0.100392701 |
| 30 | NP.854.central.ZNF426 | 0.093102006 |

TABLE 15

| | Important feature variables for MC/MS | |
| No. | Feature variable | Contribution |
| --- | --- | --- |
| 1 | MCMS.ATAC.1.9474283423837664 | 1 |
| 2 | MCMS.GCGT.5.683147383297788 | 0.980664968 |
| 3 | MCMS.TCGG.0.673454186381284 | 0.976379752 |
| 4 | MCMS.SBS33.0.0 | 0.967317343 |
| 5 | MCMS.CCGA.14.692109929470046 | 0.947452903 |
| 6 | MCMS.CCGC.1.8906672577072587 | 0.939355731 |
| 7 | MCMS.TCAA | 0.933021963 |
| 8 | MCMS.TCTA.2.7418369666693536 | 0.921852827 |
| 9 | MCMS.ATCA | 0.92134136 |
| 10 | MCMS.ACTA.2.333454005336968 | 0.9154194 |
| 11 | MCMS.CTGA | 0.910193086 |
| 12 | MCMS.SBS16 | 0.886824608 |
| 13 | MCMS.TCGG.0.4480961044108473 | 0.875262558 |
| 14 | MCMS.CCTG | 0.850984633 |
| 15 | MCMS.SBS13 | 0.849282265 |
| 16 | MCMS.ATGC | 0.848211288 |
| 17 | MCMS.GTAC | 0.842575967 |
| 18 | MCMS.ACTC.2.274719208085415 | 0.840854824 |
| 19 | MCMS.SBS34 | 0.840699196 |
| 20 | MCMS.CCAT.1313.5686331022491 | 0.838340819 |
| 21 | MCMS.CCTT.2.6087716556190585 | 0.836694241 |
| 22 | MCMS.SBS29 | 0.833842278 |
| 23 | MCMS.GCGC.6.199141903779243 | 0.833734155 |
| 24 | MCMS.CTGT | 0.830084145 |
| 25 | MCMS.SBS7a.48.8966747500918 | 0.824118853 |
| 26 | MCMS.SBS86 | 0.820313811 |
| 27 | MCMS.TCAA.5.727833482896742 | 0.819446027 |
| 28 | MCMS.TCGT | 0.818682671 |
| 29 | MCMS.CTGA.0.0259408741884836 | 0.81628412 |
| 30 | MCMS.SBS94.nan | 0.812509775 |

The multi-cancer early detection model can effectively distinguish cancer patients from healthy people. The multi-cancer early detection model has a sensitivity of 84.9% and a specificity of 99.0% in a training set and a sensitivity of 78.8% and a specificity of 99.2% in a test set, and there is no difference in results between the sets. Specific results are shown in Tables 16 to 19.

TABLE 16

| | Sensitivity performance of the multi-cancer early detection model for detection of a cancer | | |
|---|---|---|---|
| Data set | Number of samples | Sensitivity | 95% CI |
| Training set | 2328 | 84.9% | (83.4%-86.3%) |
| Test set | 1633 | 78.8% | (76.6%-80.6%) |

TABLE 17

| | Specificity performance of the multi-cancer early detection model for healthy people | | |
|---|---|---|---|
| Data set | Number of samples | Specificity | 95% CI |
| Training set | 2553 | 99.0% | (98.6%-99.3%) |
| Validation set | 1657 | 99.2% | (98.6%-99.5%) |

TABLE 18

| | | Sensitivity performance of the multi-cancer early detection model for detection of a cancer at different stages | | |
|---|---|---|---|---|
| Stage | Number of samples | Number of samples detected | Sensitivity | 95% CI |
| 0 | 46 | 28 | 60.9% | (46.5%-73.6%) |
| I | 1617 | 1334 | 82.5% | (80.6%-84.3%) |
| II | 810 | 610 | 75.3% | (72.2%-78.2%) |
| III | 712 | 597 | 83.8% | (81%-86.4%) |
| IV | 359 | 328 | 91.4% | (88%-93.9%) |
| Unknown | 417 | 364 | 87.3% | (83.7%-90.2%) |

TABLE 19

| | | Sensitivity performance of the multi-cancer early detection model for detection of various cancers | | |
|---|---|---|---|---|
| Cancer type | Number of samples | Number of samples detected | Sensitivity | 95% CI |
| Breast cancer | 244 | 128 | 52.5% | (46.2%-58.6%) |
| Cervical cancer | 103 | 85 | 82.5% | (74.1%-88.7%) |
| Intestinal cancer | 467 | 346 | 74.1% | (69.9%-77.9%) |
| Endometrial cancer | 293 | 159 | 54.3% | (48.5%-59.9%) |
| Esophageal cancer | 238 | 217 | 91.2% | (86.9%-94.2%) |
| Gastric cancer | 224 | 180 | 80.4% | (74.7%-85%) |
| Nasopharyngeal carcinoma | 153 | 110 | 71.9% | (64.3%-78.4%) |
| Liver cancer | 383 | 382 | 99.7% | (98.5%-100%) |
| Lung cancer | 1035 | 958 | 92.6% | (90.8%-94%) |
| Ovarian cancer | 118 | 111 | 94.1% | (88.3%-97.1%) |
| Pancreatic cancer | 207 | 154 | 74.4% | (68%-79.9%) |
| Prostate cancer | 197 | 149 | 75.6% | (69.2%-81.1%) |
| Cholangiocarcinoma | 94 | 93 | 98.9% | (94.2%-99.9%) |
| Lymphoma | 205 | 189 | 92.2% | (87.7%-95.1%) |

The multi-cancer TOO model can be used to allow cancer TOO tracing of a positive sample. After the training of the model is completed, a classification result is predicted with validation samples to obtain tracing probabilities for different cancers, and cancers with top 1 and 2 probability values (first/second classification) are selected for verification of an accuracy. The performance of the multi-cancer TOO model is shown in Tables 20 and 21:

TABLE 20

| Performance of the multi-cancer TOO model | | |
|---|---|---|
| | Accuracy of Top 1 | Accuracy of Top 2 |
| Training set | 68.5% | 82.3% |
| Validation set | 71.5% | 83.8% |

Specific test data is as follows:

TABLE 21

| | Performance data of the multi-cancer TOO model for different cancers | |
|---|---|---|
| Prediction by the multi-cancer TOO model | Cancer type | Sensitivity |
| Top 1 | Cholangiocarcinoma | 5.13% |
| | Breast cancer | 79.00% |
| | Cervical cancer | 35.00% |
| | Intestinal cancer | 81.64% |
| | Endometrial cancer | 84.07% |
| | Esophageal cancer | 45.74% |
| | Gastric cancer | 38.82% |
| | Liver cancer | 92.76% |
| | Lung cancer | 94.21% |
| | Lymphoma | 78.75% |
| | Head and neck cancer | 20.25% |
| | Ovarian cancer | 30.43% |
| | Pancreatic cancer | 32.10% |
| | Prostate cancer | 76.47% |
| Top 2 | Cholangiocarcinoma | 46.15% |
| | Breast cancer | 91.00% |
| | Cervical cancer | 42.50% |
| | Intestinal cancer | 95.17% |
| | Endometrial cancer | 93.81% |
| | Esophageal cancer | 80.85% |
| | Gastric cancer | 62.35% |
| | Liver cancer | 96.05% |
| | Lung cancer | 98.15% |
| | Lymphoma | 83.75% |
| | Head and neck cancer | 40.51% |
| | Ovarian cancer | 41.30% |
| | Pancreatic cancer | 58.02% |
| | Prostate cancer | 88.24% |

The method of the present disclosure can classify different cancers, and then can conduct reasonable selection in combination with relevant clinical actual indicators clinically.

What is claimed is:

1. A method for constructing a multi-cancer early detection model, wherein the multi-cancer early detection model is used to distinguish cancer patients of a plurality of cancers from healthy people; and the method comprises the following steps:

step 1, extracting cfDNAs from samples of a positive group and a control group, and sequencing to obtain read data;

step 2, aligning the read data to a reference genome, dividing the reference genome into a plurality of windows, and acquiring proportions of short reads and long reads in each of the plurality of windows as a first feature set;

step 3, aligning the read data to the reference genome, and with long arms and short arms of chromosomes as regional ranges, acquiring quantities of reads in different length gradient intervals in each of the regional ranges as a second feature set, wherein the different length gradient intervals refer to different length gradient ranges produced by increasing at a set step size progressively in a range of 100 bp to 220 bp, and the long arms and the short arms are selected from the group consisting of the following chromosome arms:

chr1_p, chr4_q, chr8_p, chr11_q, chr16_q, chr20_p, chr1_q, chr5_p, chr8_q, chr12_p, chr17_p, chr20_q, chr2_p, chr5_q, chr9_p, chr12_q, chr17_q, chr21_q, chr2_q, chr6_p, chr9_q, chr13_q, chr18_p, chr22_q, chr3_p, chr6_q, chr10_p, chr14_q, chr18_q, chr3_q, chr7_p, chr10_q, chr15_q, chr19_p, chr4_p, chr7_q, chr11_p, chr16_p, and chr19_q, wherein a character chr+a number behind the character chr represents a chromosome number, q represents a long arm, and p represents a short arm;

step 4, dividing the reference genome into a plurality of windows, and acquiring copy number data in different ones of the plurality of windows on the chromosomes in WGS data as a third feature set;

step 5, acquiring transcription factors from a GTRD, and excluding transcription factors without a known transcription site in a CIS-BP database;

with a range of −5 kb to +5 kb from a transcription site of each remaining transcription factor as a window, acquiring fragments with a length of 100 bp to 220 bp capable of being aligned to the window, and conducting GC correction and sequencing depth smoothing successively on read data in the window to obtain a profile curve of each remaining transcription factor; and for each remaining transcription factor, acquiring three feature sets together as a fourth feature set as follows:

1) for all transcription sites of each remaining transcription factor, calculating an average depth from 1 kb at an upper end to 1 kb at a lower end of each of the transcription sites;

2) for the profile curve, calculating an amplitude value of a curve trough as a central depth of each remaining transcription factor; and 3) conducting fast Fourier transform on the profile curve to obtain an amplitude value of a peak point of a nucleosome amplitude signal;

step 6, 1) counting reads of NCG motifs and CGN motifs at breaks in broken CpG sites and proportions of the reads; and 2) counting reads of NCG, CGN, CGC, and GCG motifs at breaks in two tandem broken CpG dinucleotide sites and proportions of the reads, and combining the reads and the proportions of the reads to obtain a fifth feature set;

step 7, acquiring single-base mutation information on the cfDNAs, and further acquiring 96 SBSs of tribase motifs and contexts of the 96 SBSs as MCs in the case of removing SNPs; acquiring the single-base mutation information on the cfDNAs, further acquiring 96 SBSs of the tribase motifs and contexts of the 96 SBSs in the case of not removing the SNPs, and conducting NMF to obtain MSs; and combining the MCs and the MSs to obtain a sixth feature set; and step 8, taking the first feature set, the second feature set, the third feature set, the fourth feature set, the fifth feature set, and the sixth feature set as initial eigenvalues, inputting the initial eigenvalues as model eigenvectors into a convolutional neural network (CNN) to obtain convolutional base models of the six features, respectively, and conducting 2nd-level meta-learning based on a cancer developing probability result output by each of the convolutional base models of the six features to generate the multi-cancer early detection model, wherein an importance of the six features is predicted based on an analysis of a gradient of an output of the CNN of the multi-cancer early detection model relative to the input initial eigenvalues, eigenvalues with top contributions in each feature set are selected as input vectors for the convolutional base models, wherein the multi-cancer early detection model is used to distinguish cancer patients from healthy people and further in patients with known cancers distinguish between cancers simultaneously.

2. The method for constructing the multi-cancer early detection model according to claim 1, wherein the step 2 comprises:

step 2-1, dividing the reference genome into the plurality of windows, and acquiring quantities of the short reads and the long reads in each of the plurality of windows; and step 2-2, normalizing the quantities of the short reads and the long reads in all the plurality of windows of the step 2-1, and taking the proportions of the short reads and the long reads produced after the normalizing as the first feature set;

the plurality of windows in the step 2-1 each have a size of 5 Mb;

the short reads each have a length of 100 bp to 150 bp and the long reads each have a length of 151 bp to 220 bp;

in the step 3, the set step size is 4 bp; and the plurality of windows in the step 4 each have a size of 1 Mb.

3. The method for constructing the multi-cancer early detection model according to claim 1, wherein the multi-cancer early detection model is further used to allow TOO-based classification of cancers in the cancer patients of the plurality of cancers; and the method further comprises:

step 9, taking the first feature set, the second feature set, the third feature set, the fourth feature set, the fifth feature set, and the sixth feature set as the initial eigenvalues, inputting the initial eigenvalues as the model eigenvectors into different classifier models, and training the different classifier models to obtain a plurality of subclassifier models for the first feature set, the second feature set, the third feature set, the fourth feature set, the fifth feature set, and the sixth feature set, respectively; and conducting stacking on the plurality of subclassifier models to obtain a TOO-based classification model, wherein the different classifier models are one or more selected from the group consisting of a generalized linear regression model, a gradient boosting machine (GBM), a random forest (RF) model, a deep learning (DL) neural network model, and an extreme gradient boosting (XGBoost) model; and a generalized linear model (GLM) is adopted for the stacking.

4. The method for constructing the multi-cancer early detection model according to claim 1, wherein the plurality of cancers are selected from the group consisting of cholangiocarcinoma, breast cancer, cervical cancer, intestinal cancer, endometrial cancer, esophageal cancer, gastric cancer, nasopharyngeal carcinoma, lung cancer, liver cancer, lymphoma, ovarian cancer, pancreatic cancer, and prostate cancer.

* * * * *